United States Patent
Diggett et al.

(10) Patent No.: US 12,406,774 B2
(45) Date of Patent: Sep. 2, 2025

(54) REMOTE SCANNING AND VALIDATING OF CLINICAL ORDER DEVICE CONFIGURATIONS

(71) Applicant: CareFusion 303, Inc., San Diego, CA (US)

(72) Inventors: Lisa Diggett, Overland Park, KS (US); Michael K. Workman, Carlsbad, CA (US); Claire Ellen Knight, Arlington, TX (US); Joshua Jay Harman, Seguin, TX (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 18/864,504

(22) PCT Filed: May 10, 2022

(86) PCT No.: PCT/US2022/028619
§ 371 (c)(1),
(2) Date: Nov. 8, 2024

(87) PCT Pub. No.: WO2023/219607
PCT Pub. Date: Nov. 16, 2023

(65) Prior Publication Data
US 2025/0166852 A1    May 22, 2025

(51) Int. Cl.
*G16H 70/40*    (2018.01)
*G06V 10/75*    (2022.01)
(Continued)

(52) U.S. Cl.
CPC .......... *G16H 70/40* (2018.01); *G06V 10/751* (2022.01); *G06V 10/945* (2022.01);
(Continued)

(58) Field of Classification Search
CPC ........ G16H 70/40; G16H 20/17; G16H 40/63; G06V 10/751; G06V 10/945;
(Continued)

(56) References Cited

U.S. PATENT DOCUMENTS

2014/0180711 A1    6/2014    Kamen et al.
2015/0379237 A1*  12/2015   Mills ...................... G16H 20/17

FOREIGN PATENT DOCUMENTS

AU    2020277098 B2 *  1/2023   .............. A61J 3/002
CN    105210104 A      12/2015
(Continued)

OTHER PUBLICATIONS

International Preliminary Report on Patentability from the International Preliminary Examining Authority for Application No. PCT/US2022/028619, dated Apr. 4, 2024, 22 pages.
(Continued)

*Primary Examiner* — Joshua B Blanchette

(57) ABSTRACT

A system for scanning and validating clinical order device configurations is disclosed. A test instance of an infusion device is created based on a request, and an automated programming command is transmitted to the test instance.
(Continued)

The automated programming command includes validation information for validating clinical order data, and a programming response is generated by the test instance based on the automated programming command, and provided for storage in a records system. In some implementations, the response includes an image, or reference to the image, of a graphical user interface that would be presented by the infusion device configured according to the validation information.

20 Claims, 12 Drawing Sheets

(51) Int. Cl.
*G06V 10/94* (2022.01)
*G06V 10/98* (2022.01)
*G06V 30/12* (2022.01)
*G06V 30/19* (2022.01)
*G06V 30/30* (2022.01)
*G16H 20/17* (2018.01)
*G16H 40/63* (2018.01)

(52) U.S. Cl.
CPC .......... *G06V 10/987* (2022.01); *G06V 30/127* (2022.01); *G06V 30/19013* (2022.01); *G06V 30/30* (2022.01); *G16H 20/17* (2018.01); *G16H 40/63* (2018.01)

(58) Field of Classification Search
CPC .............. G06V 10/987; G06V 30/127; G06V 30/19013; G06V 30/30
See application file for complete search history.

(56) References Cited

FOREIGN PATENT DOCUMENTS

| CN | 105229694 A | 1/2016 | |
|---|---|---|---|
| CN | 112106142 A | 12/2020 | |
| EP | 2795492 B1 | 12/2021 | |
| WO | WO-2014100736 A2 * | 6/2014 | ............ G16H 20/10 |
| WO | WO-2016004088 A1 | 1/2016 | |
| WO | WO-2022109042 A1 | 5/2022 | |

OTHER PUBLICATIONS

International Search Report and Written Opinion for Application No. PCT/US2022/028619, dated Jan. 4, 2023, 22 pages.
Australian Office Action for Application No. 2022458180, dated Dec. 12, 2024, 8 pages.
Canadian Office Action for Application No. 3,256,782, May 6, 2025, 9 pages.
Chinese Office Action for Application No. 202280095813.6, dated Apr. 10, 2025, 12 pages including machine translation.

* cited by examiner

| Guardrails Drug Setup |
| Ⓐ Dopamine |

| Drug Amount | 2 gram |
| Diluent Volume | 50 mL |
| Patient Weight | Not Used |
| Time Units | Min |
| Dosing Units | mcg/min |

[Conc]: 40 mcg/mL

>Press NEXT to Confirm

| Drug Library | Next |

| Guardrails Drug Setup |
| Ⓐ Dopamine |

Continuous Infusion

| Rate | 7.5 mL/h |
| VTBI | 50 mL    Available: (50 mL) |
| Dose | 5 mcg/min |

[Conc]: 40 mcg/mL

>Press START

| Delay Options | Setup | Bolus | Start |

Midtown Hospital
Adult ICU

A   Dopamine
    5 mcg/min

B

Patient ID: 1234567891

| Volume Infused | Audio Adjust |

FIG. 6C

| A | Guardrails Drug Setup
Lidocaine |

Dose Exceeds
Guardrail Limit Of
8 mg/min.
Proceed?

Yes

No

>Press Yes or No

FIG. 6D

REMOTE SCANNING AND VALIDATING OF CLINICAL ORDER DEVICE CONFIGURATIONS

CROSS-REFERENCE TO RELATED APPLICATION

This is a National Stage Application filed under 35 U.S.C. 371 based on International Patent Application No. PCT/US22/28619, filed on May 10, 2022, the disclosure of which is incorporated herein by reference in their entireties.

TECHNICAL FIELD

This application relates generally to ensuring that an infusion device is properly programmed.

BACKGROUND

Modern infusion devices provide, via a user interface, manual workflows with regard to programming the pumps for medication infusions. Also, an infusion device may receive infusion order parameters from a third-party system to configure the device's pump to deliver a specific fluid, at specific rates, for a specific patient; a remote programming command often referred to as an automated programming request (APR). The APR configuration may include pre-populating operating parameter values for presentment via the user interface.

Pre-population of infusion parameters reduces the number of programming screens, key presses, and potential input errors that may exist with manual programming. Generally, there may be no differences in programming screens, prompts or the user interface between systems configured for APR and those that are not, and the implementation of APRs does not preclude a clinician from manually programming the pump. However, manual programming is required in the event of a failure in any component of the interfaced system.

In some APR enabled systems, APR orders may be rejected due to device to order deviations that prevent the system from taking automatic action based on the order. For example, an infusion device may be configured to not infuse at a flow rate greater than 999 mL/h. If the APR order includes a rate parameter value of 1000 mL/h, then the order may be rejected because the auto-programmed parameter value is misaligned with the pump configuration. When an order is rejected, the device must be programmed manually to initiate the infusion. Misalignment errors are not often discovered until the pump is being programmed in a clinical setting for delivery of an infusate to a patient. Such APR related errors are not known to be centrally catalogued.

SUMMARY

The subject technology provides a mechanism and corresponding algorithm that for scans clinical order device configurations and identifies APR misalignment errors in APR orders. Unlike legacy systems and processes, misalignments between pharmacy and other hospital information systems and infusion pumps may be discovered in real time and across multiple devices in a health care network, and catalogued in a central database. Accordingly, drug libraries and/or other medication databases may be updated with "good" data according to a centralized plan, thereby removing misaligned data that would otherwise cause devices to be taken out of service for manual correction by a clinician or technician.

In this regard, the subject technology includes a system for remote scanning and validating clinical order device configurations, comprising: a processor; and a non-transitory computer-readable medium including instructions that, when executed by the processor, cause the system to: receive a request for a test instance of an infusion device; cause the test instance to be created based on the request; cause an automated programming command to be transmitted to the identified test instance, the automated programming command including validation information for validating clinical order data; generate, based on the automated programming command being transmitted to the test instance, a programming response including an image, or reference of the image, of a graphical user interface that would be presented by the infusion device configured according to the validation information; and provide the programming response for storage in a records system. Other aspects include corresponding devices, methods, and computer program products for implementation of the corresponding system and its features.

The subject technology also relates to a method for remote scanning and validating clinical order device configurations, comprising: transmitting, to a server, a request for a test instance of an infusion device; receiving, from the server in response to the request, an identifier of the test instance; identifying clinical order data associated with a medication; causing an automated programming command to be transmitted, based on the identifier, to the test instance to validate the identified clinical order data; receiving, based on the automated programming command being transmitted to the test instance, a programming response including an image, or reference of the image, of a graphical user interface that would be presented by the infusion device based on the infusion device processing the automated programming command; identifying an error in the clinical order data based on the programming response; and providing the programming response for storage in a records system. Other aspects include corresponding systems, apparatus, and computer program products for implementation of the corresponding method and its features.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Description of Implementations below, in conjunction with the following drawings. Like reference numerals refer to corresponding parts throughout the figures and description.

FIGS. 6A, 6B, and 6C depict a series of user interfaces in an example infusion programming workflow for automated programming an infusion device, according to various aspects of the subject technology.

FIG. 6D depicts an example user interface in which an automated programming request resulted in an error, according to various aspects of the subject technology.

DESCRIPTION

Reference will now be made to implementations, examples of which are illustrated in the accompanying drawings. In the following description, numerous specific details are set forth in order to provide an understanding of the various described implementations. However, it will be apparent to one of ordinary skill in the art that the various described implementations may be practiced without these specific details. In other instances, well-known methods, procedures, components, circuits, and networks have not been described in detail so as not to unnecessarily obscure aspects of the implementations.

Figure 1A:
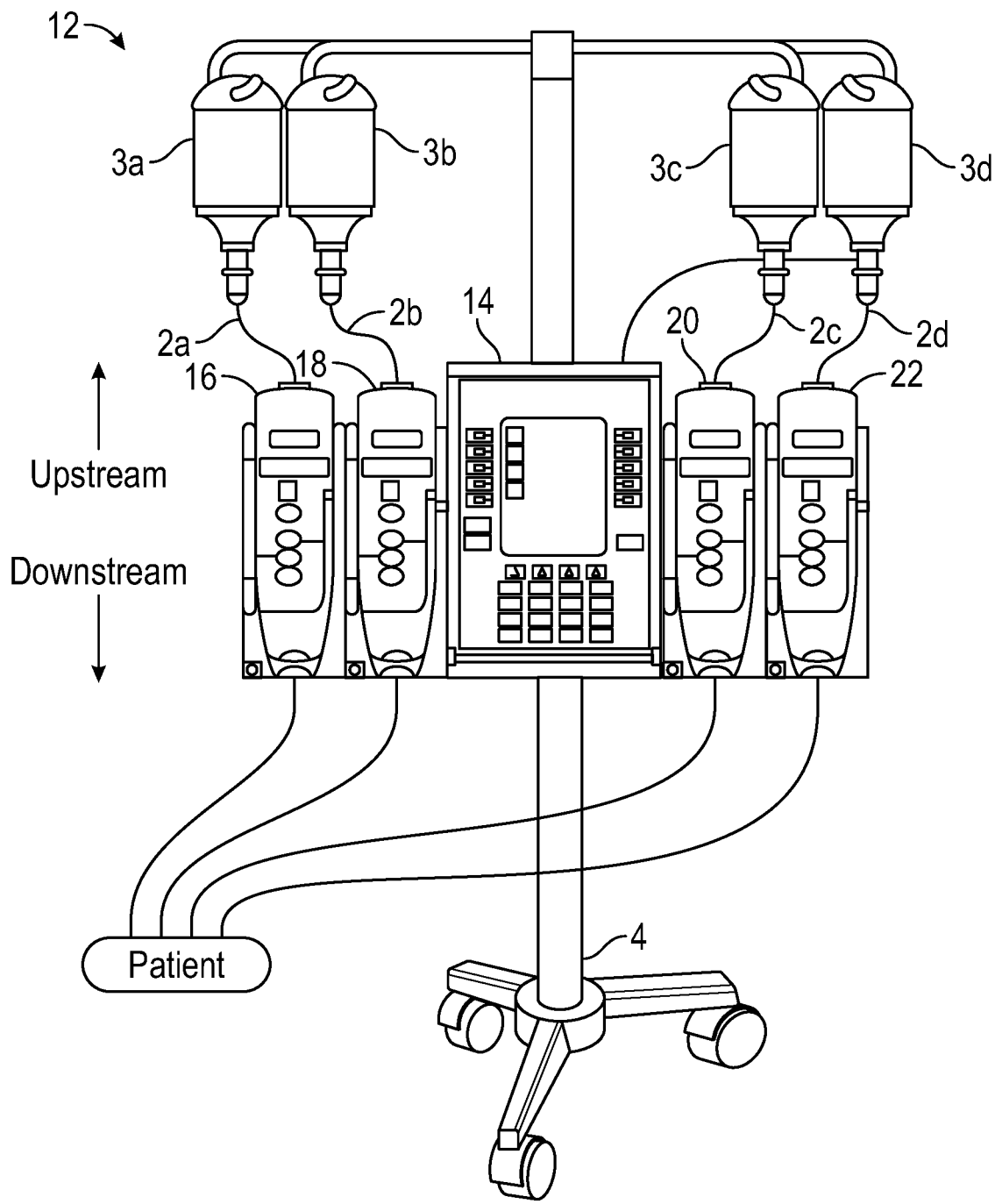
FIG. 1A depicts an example patient care system that includes an infusion device.

FIG. 1A is an example patient care system, according to various aspects of the subject technology. The patient care system 1 shown in FIG. 1A includes four fluid infusion pumps 16, 18, 20, 22, each of which is in operative engagement with a respective fluid administration set 2a-d. Fluid supplies 3a-d, which may take various forms but in this case are shown as bottles, are inverted and suspended above the pumps. Fluid supplies may also take the form of bags or other types of containers. Both the patient care system 1 and the fluid supplies 3a-d are mounted to a roller stand or pole 4. The specific fluid supplies as well as their orientation (e.g., mount location, mount height, mounting type, etc.) within the care area may generate one or more interaction records. The interaction record for a set for example may be generated in part by detecting a scannable code associated with the set or detecting a physical structure on the set that encodes identifying information for the set prior to use.

As shown in the example implementation of FIG. 1A, each administration set 2a-d is connected between a respective fluid supply 3a-d and the same patient so that the patient may receive the fluids in all the fluid supplies. The administration set may be identified either actively by, for example, scanning by a clinician or passively by, for example, wireless or optical detection of the administration set.

In the depicted example, a separate infusion pump 16, 18, 20, 22 is used to infuse each of the fluids of the fluid supplies into the patient. The infusion pumps are flow control devices that will act on the respective tube or fluid conduit of the fluid administration set to move the fluid from the fluid supply through the conduit to the patient. Because individual pumps are used, each may be individually set to the pumping or operating parameters required for infusing the particular medical fluid from the respective fluid supply into the patient at the particular rate prescribed for that fluid by the clinician.

Typically, medical fluid administration sets have more parts than are shown in FIG. 1A. Many have check valves, drip chambers, valved ports, connectors, and other devices well known to those skilled in the art. These other devices have not been included in the drawings so as to preserve clarity of illustration.

Figure 1B:
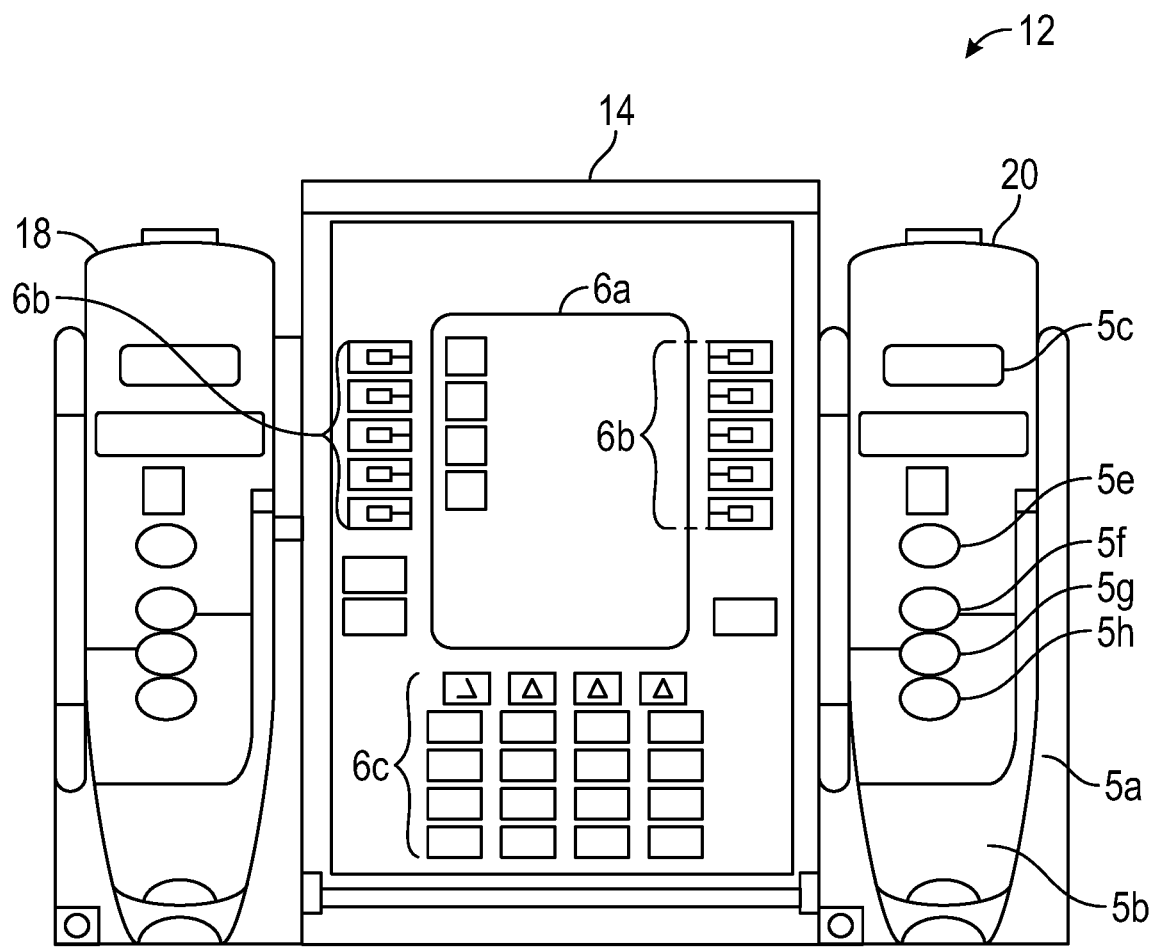
FIG. 1B depicts a closer view of a portion of the patient care system shown in FIG. 1A.

FIG. 1B is a closer view of a portion of the example patient care system shown in FIG. 1A, according to various aspects of the subject technology. FIG. 1B shows two of the fluid infusion pumps mounted at either side of a programming module, and the displays and control keys of each, with the programming module being capable of programming both infusion pumps. The infusion device 12 includes a door 5a and a handle 5b that operates to lock the door in a closed position for operation and to unlock and open the door for access to the internal pumping and sensing mechanisms and to load administration sets for the pump. When the door 5a is open, the tube can be connected with the pump 20. When the door 5a is closed, the tube is brought into operating engagement with the pumping mechanism, the upstream and downstream pressure sensors, and the other equipment of the pump. A display 5c, such as an LED display, is located in plain view on the door in this embodiment and may be used to visually communicate various information relevant to the pump 20, such as alert indications (e.g., alarm messages). Control keys 5e-h exist for programming and controlling operations of the infusion pump as desired. In some implementations, the control keys may be presented as interactive elements on the display 5c (e.g., touchscreen display). The infusion device 12 and/or infusion pump 20 may also include audio alert equipment in the form of a speaker (not shown).

The programming module 14 of the infusion device 12 includes a display 6a for visually communicating various information, such as the operating parameters of a connected pump and alert indications and alert messages. The programming module 14 may also include a speaker to provide audible alerts. In some implementations, the display 6a may be implemented as a touchscreen display. In such implementations, the control keys 6b may be omitted or reduced in number by providing corresponding interactive elements via a graphical user interface presented via the display 6a. The programming module 14 may include a communications system (not shown) with which the programming module 14 may communicate with external equipment such as a medical facility server or other computer and with a portable processor, such as a handheld communication device or a laptop-type of computer, or other information device that a clinician may have to transfer information as well as to download drug libraries to a programming module 16, 18, 20, 22 (such as pump 20). The communication module may be used to transfer access and interaction information for clinicians encountering the programming module or device coupled therewith (e.g., pump 20 or bar code scanner). The communications system may include one or more of a radio frequency (RF) system, an optical system such as infrared, a BLUETOOTH™ system, or other wired or wireless system. The bar code scanner and communications system may alternatively be included integrally with the infusion pump 20, such as in cases where a programming module is not used, or in addition to one with the programming module 14. Further, information input devices need not be hard-wired to medical instruments, information may be transferred through a wireless connection as well. Additionally, other types of modules may be connected to the pump modules or to the programming module such as a syringe pump module, patient controlled analgesic module, End Tidal CO2 monitoring module, oximeter monitoring module, or the like.

In some embodiments, the pressure measurements from the upstream and/or downstream pressure sensors are transmitted to a server or other coordination device, and the methods disclosed herein are implemented on the server or other coordination device. For example, more sophisticated and computationally intensive approaches like machine-learning can be implemented on the server (or on a PCU with a larger memory and/or CPU resources). In some embodiments, machine learning is used to identify empty conditions based on pressure signals received from the pump.

Figure 1C:
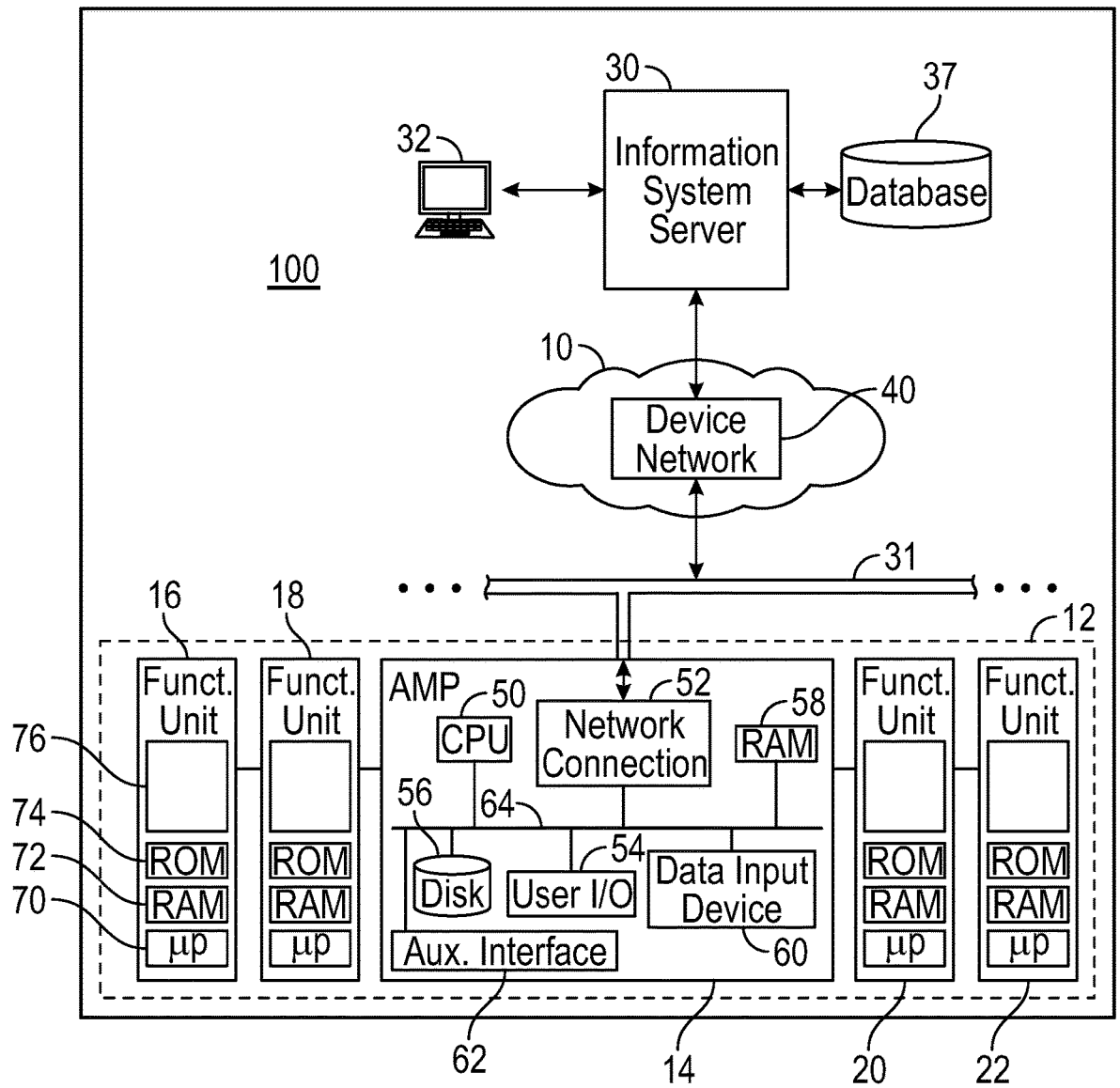
FIG. 1C depicts an example of an institutional patient care system of a healthcare organization, according to aspects of the subject technology.

FIG. 1C depicts an example of an institutional patient care system 100 of a healthcare organization, according to aspects of the subject technology. In FIG. 1C, a patient care device (or "medical device" generally) 12 is connected to a hospital network 10. The term patient care device (or "PCD") may be used interchangeably with the term patient care unit (or "PCU"), either which may include various ancillary medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each element 12 is connected to an internal healthcare network 10 by a transmission channel 31. Transmission channel 31 is any wired or wireless transmission channel, for example an 802.11 wireless local area network (LAN). In some implementations, network 10 also includes computer systems located in various departments throughout a hospital. For example, network 10 of FIG. 1C optionally includes computer systems associated with an admissions department, a billing department, a biomedical engineering department, a clinical laboratory, a central supply department, one or more unit station computers and/or a medical decision support system. As described further below, network 10 may include discrete subnetworks. In the depicted example, network 10 includes a device network 41 by which patient care devices 12 (and other devices) communicate in accordance with normal operations.

Additionally, institutional patient care system 100 may incorporate a separate information system server 30. Moreover, although the information system server 30 is shown as a separate server, the functions and programming of the information system server 30 may be incorporated into another computer, if such is desired by engineers designing the institution's information system. Institutional patient care system 100 may further include one or multiple device terminals 32 for connecting and communicating with information system server 30. Device terminals 32 may include personal computers, personal data assistances, and mobile devices such as laptops, tablet computers, augmented reality devices, or smartphones, configured with software for communications with information system server 30 via network 10.

Patient care device 12 comprises a system for providing patient care, such as that described in Eggers et al., which is incorporated herein by reference for that purpose. Patient care device 12 may include or incorporate pumps, physiological monitors (e.g., heart rate, blood pressure, ECG, EEG, pulse oximeter, and other patient monitors), therapy devices, and other drug delivery devices may be utilized according to the teachings set forth herein. In the depicted example, patient care device 12 comprises a control module 14, also referred to as interface unit 14, connected to one or more functional modules 116, 118, 120, 122. Interface unit 14 includes a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Interface unit 14 also, although not necessarily, includes a main non-volatile storage unit 56, such as a hard disk drive or non-volatile flash memory, for storing software and data and one or more internal buses 64 for interconnecting the aforementioned elements.

In various implementations, user interface device 54 is a touch screen for displaying information to a user and allowing a user to input information by touching defined areas of the screen. Additionally, or in the alternative, user interface device 54 could include any means for displaying and inputting information, such as a monitor, a printer, a keyboard, softkeys, a mouse, a track ball and/or a light pen. Data input device 60 may be a bar code reader capable of scanning and interpreting data printed in bar coded format. Additionally or in the alternative, data input device 60 can be any device for entering coded data into a computer, such as a device(s) for reading a magnetic strips, radio-frequency identification (RFID) devices whereby digital data encoded in RFID tags or smart labels (defined below) are captured by the reader 60 via radio waves, PCMCIA smart cards, radio frequency cards, memory sticks, CDs, DVDs, or any other analog or digital storage media. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1C to be disposed within interface unit 14, it is recognized that data input device 60 may be integral within pharmacy system 34 or located externally and communicating with pharmacy system 34 through an RS-232 serial interface or any other appropriate communication means. Auxiliary interface 62 may be an RS-232 communications interface, however any other means for communicating with a peripheral device such as a printer, patient monitor, infusion pump or other medical device may be used without departing from the subject technology. Additionally, data input device 60 may be a separate functional module, such as modules 16, 18, 20 and 22, and configured to communicate with controller 14, or any other system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. Any direct or indirect network connection may be used, including, but not limited to a telephone modem, an MIB system, an RS232 interface, an auxiliary interface, an optical link, an infrared link, a radio frequency link, a microwave link or a WLANS connection or other wireless connection.

Functional modules 16, 18, 20, 22 are any devices for providing care to a patient or for monitoring patient condition. As shown in FIG. 1C, at least one of functional modules 16, 18, 20, 22 may be an infusion pump module such as an intravenous infusion pump for delivering medication or other fluid to a patient. For the purposes of this discussion, functional module 116 is an infusion pump module. Each of functional modules 16, 18, 20, 22 may be any patient treatment or monitoring device including, but not limited to, an infusion pump, a syringe pump, a PCA pump, an epidural pump, an enteral pump, a blood pressure monitor, a pulse oximeter, an EKG monitor, an EEG monitor, a heart rate monitor, an intracranial pressure monitor, or the like. Functional module 16, 18, 20 and/or 22 may be a printer, scanner, bar code reader, near-field communication reader, RFID reader, or any other peripheral input, output or input/output device.

Each functional module 16, 18, 20 and/or 22 communicates directly or indirectly with interface unit 14, with interface unit 14 providing overall monitoring and control of device 12. Functional modules 16, 18, 20 and/or 22 may be connected physically and electronically in serial fashion to one or both ends of interface unit 14 as shown in FIG. 1C, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control unit 14. As described above, additional medical devices or peripheral devices may be connected to patient care device 12 through one or more auxiliary interfaces 62.

Each functional module 16, 18, 20, 22 may include module-specific components 76, a microprocessor 70, a volatile memory 72 and a nonvolatile memory 74 for storing information. It should be noted that while four functional modules are shown in FIG. 1C, any number of devices may be connected directly or indirectly to central controller 14. The number and type of functional modules described herein are intended to be illustrative, and in no way limit the scope of the subject technology. Module-specific components 76 include any components necessary for operation of a particular module, such as a pumping mechanism for infusion pump module 116.

While each functional module may be capable of a least some level of independent operation, interface unit 14 monitors and controls overall operation of device 12. For example, as will be described in more detail below, interface unit 14 provides programming instructions to the functional modules 16, 18, 20, 22 and monitors the status of each module.

Medical devices incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

Data to and from the various data sources can be converted into network-compatible data with existing technology, and movement of the information between the medical device and network can be accomplished by a variety of means. For example, patient care device 12 and network 10 may communicate via automated interaction, manual interaction or a combination of both automated and manual interaction. Automated interaction may be continuous or intermittent and may occur through direct network connection 54 (as shown in FIG. 1C), or through RS232 links, MIB systems, RF links such as BLUETOOTH, IR links, WLANS, digital cable systems, telephone modems or other wired or wireless communication means. Manual interaction between patient care device 12 and network 10 involves physically transferring, intermittently or periodically, data between systems using, for example, user interface device 54, coded data input device 60, bar codes, computer disks, portable data assistants, memory cards, or any other media for storing data. The communication means in various aspects is bidirectional with access to data from as many points of the distributed data sources as possible. Decision-making can occur at a variety of places within network 10. For example, and not by way of limitation, decisions can be made in health information system (HIS) server 30, decision support 48, remote data server 49, hospital department or unit stations 46, or within patient care device 12 itself.

All direct communications with medical devices operating on a network in accordance with the subject technology may be performed through information system server 30, known as the remote data server (RDS). In accordance with aspects of the subject technology, network interface modules incorporated into medical devices such as, for example, infusion pumps or vital signs measurement devices, ignore all network traffic that does not originate from an authenticated RDS. The primary responsibilities of the RDS of the subject technology are to track the location and status of all networked medical devices that have NIMs, and maintain open communication.

According to various implementations, server 30 includes a formulary and/or pharmacy information system. Pharmacy information systems may enable a safer physician medication order process. A pharmacy website (e.g., provided by the server) may provide the physician with a list of available drugs from which the physician may select. The pharmacy website may contain a drug library having the list of available drugs but may also contain and present to the physician the drug names associated with recommended dosages and dose limits that have been established or adopted by the healthcare facility. In such a case where the physician need only select items from the computer screen rather than having to manually type in drug names and drug administration numbers (such as infusion rates, times, etc.) associated with administration of the medication, a more accurate medication process should result.

If a clinical order is for administration of a particular medication regimen, the order will be transmitted to the facility's pharmacy information system 30. The pharmacy reviews the order, and once the order has been prepared, the order may be transmitted to the nurse station for matching with the appropriate patient. Formulary is an approved list of drugs for use (e.g., available to order for a patient) within a medical facility. Within a formulary, there may be indication for use information and/or concentrations and drug ranges approved for the facility. As will be described further, a formulary may be used to define one or more medical device drug libraries, which may then be provided to infusion pumps within a hospital network. Inside the library, there is medication information such as drug names, concentration, diluent volume, strength, minimum or maximum infusion parameters for a drug, and other parameters. The formulary's establishment of these parameters, along with parameters for off-formulary orders, via the system 30 is useful for maintaining consistency across the healthcare environment and ensuring an order is intelligible and executed according to expectations by other devices within the system 30 (e.g., an infusion pump).

With further reference to FIG. 1C, patient care device 12 is capable of operating in several different modes, or personalities, with each personality defined by a configuration database. The configuration database may be a database 56 internal to patient care device, or an external database 37. A particular configuration database is selected based, at least in part, by patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information also includes care provider information (e.g., physician identification) or a patient care device's 12 location in the hospital or hospital computer network. Patient care information may be entered through interface device 52, 54, 60 or 62, and may originate from anywhere in network 10, such as, for example, from a pharmacy server, admissions server, laboratory server, and the like.

A memory 56, 58 of the interface unit 14 may contain a drug library or libraries, an event log or logs, and pump configuration settings, such as, but not limited to, profiles to be used in particular practice areas such as ICU, PED, etc. The memory may be electronically loadable memory such as non-volatile memory (e.g., EEPROM). Drug libraries stored on pumps (which illustratively contain such information as the drug names, ranges of delivery parameter values such as proper concentrations, dosage units, and dose limits) can be used to perform drug calculation-based infusions in a clinical setting.

A drug library stored within the pump's memory may include clinical order settings such as limits set by the clinical institution for each drug of the library (also termed as "guardrails" herein). Such limits may take the form of maximum and minimum dosages for each drug which may be made dependent on patient factors or other factors associated with delivery of the drug. For example, the dosage limits may vary depending on the weight of the patient or body surface area ("BSA"), depending on the unit or ward of the medical institution in which the drug is being used (for example neonatal care unit (NCU), the intensive care unit (ICU), etc.), and depending on other factors. An alarm may be provided if the nurse sets the pump to operate outside the range between the limits for a particular drug. In some cases, the alarm may be overridden and in other cases it may not. The medical facility may establish "soft" limits for each drug, which may be overridden by the nurse, and "hard" limits which may not. In either case where a limit is exceeded, a pump data log or other processor in communication with the infusion pump may record each such limit event for later analysis where the attempted setting is higher than the maximum or lower than the minimum dosage.

The pump also includes a display for displaying a user interface, including a control panel through which the user can program the programmable controller and a display screen for displaying drug entries from the drug library. Each of the associated sets of drug delivery parameters includes information selected from a group of parameters including drug concentration, drug delivery rate, drug dose, and bolus size. The electronically loaded drug library contains a list of available mode options specifying the units available for expressing drug delivery information, and the drug infusion pump offers the user the list of available mode options from which to make a selection when the electronically loaded drug library is in the pump. In the case of a syringe pump, the electronically loaded drug library may include a list of names of syringe manufacturers identifying syringes that can be used in the drug infusion pump, and the drug infusion pump offers the user the list of names of syringe manufacturers from which to make a selection when the electronically loaded drug library is in the pump. The loaded drug library may include a list of syringe sizes identifying syringes that can be used in the drug infusion pump, and the drug infusion pump offers the user the list of syringe sizes from which to make a selection when the electronically loaded drug library is in said pump. In the case of a peristaltic pump, the electronically loaded drug library may include a list of infusion set manufacturers. A loaded drug library may include a set of features, each of which is either be toggled on or off, and the pump offers the user only the features from among the set of features that are toggled on when the electronically loaded drug library is in said pump.

Figure 2:
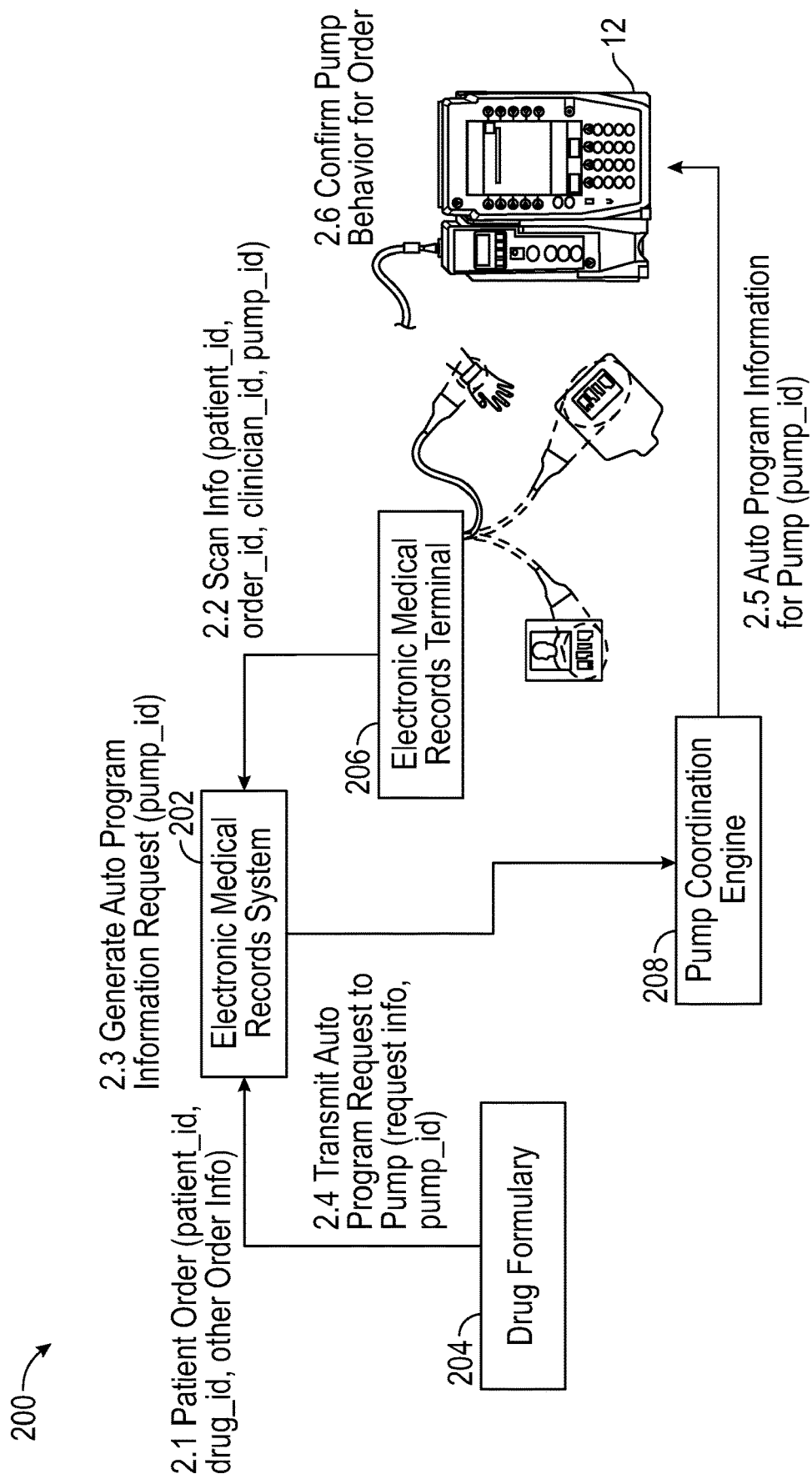
FIG. 2 depicts an example system for reviewing and verifying formularies, according to aspects of the subject technology.

FIG. 2 depicts an example system 200 for reviewing and verifying formularies, according to aspects of the subject technology. Interoperability between a hospital's electronic medical records (EMR) 202 and medical devices such as infusion device 12 enable pre-population of infusion parameters. Pre-population of infusion parameters may reduce the number of programming screens and key presses required with manual programming of a pump. The implementation of interoperability does not preclude a clinician from manually programming the infusion device. Manual programming may be required in the event of a failure in any component of the interfaced system.

A formulary 204 determines which medications can be dispensed within a hospital network. A hospital committee may be formed to determine how medications within that formulary would be applied to the patient care devices 12. Configuration definitions (e.g., by hospital unit such as ICU, NICU, Pediatrics, Oncology, Surgery, etc.) are agreed upon and the drugs and typical infusion protocols are established in a medical device drug library ("drug library"). In addition, all outer limit, or guard rail, conditions are defined in the drug library. When all of the definitions are complete, then a configuration can be released (2.1) including the drug library. Pumps at the institution are then updated by transferring the configuration databases into some or all of their pumps.

In the clinical field, a clinician may scan a medical item such as an infusate package using a scanner associated with a medical device such as an infusion device 12. For example, a bar code reader (or other data input device) is used to scan the coded drug label, the patient's coded ID band and the caregiver's ID badge, and optionally supplementary prescription information or medical device configuration instructions (including configuration database ID) printed on the label or an accompanying order. The reader/scanner is not required to be integrated with a medical device. The scanner may be part of a separate device such as a medical records terminal 206 (e.g., part of one or more computing devices) connected to the same network 40 as the infusion device 12 and configured with software to function in an overall workflow involving the infusion device 12. The scanning initiates a process by which information pertaining to the item (e.g., scanned from a code affixed to or transmitted by the item) is automatically sent (2.2) to the hospital's EMR 202 (e.g., at a centralized server 30) via a network 40. The EMR 202 performs certain actions pertaining to the item and generates (2.3) and sends an automated programming request (APR) to the medical device 12 to load parameters pertaining to the item. The parameters may be stored in the medical device 12, but loaded in response to an identifier received from the server. While the examples herein involve an infusion device, any medical device may be configured in the same or similar manner and employ the automated programming error mitigation described herein.

In the depicted implementation, a coordination engine 208 coordinates messages sent from the EMR 202 to the infusion device 12. In the depicted implementation, the EMR 202 transmits an APR (2.4) to the pump coordination engine 206 with a device identifier (ID) of the infusion device to receive the APR. The coordination engine then determines whether the infusion device 12 identified by the EMR is available and, if so, forwards the APR to the device 12 (2.5). When an APR received by an infusion device 12, the infusion device 12 determines whether the APR and content are compliant. The compliance determination may be based whether the data fields included in the APR are congruent with a drug library loaded in the infusion device. For example, the APR may include or omit a field that may prevent the device 12 from parsing or auto-programming itself using the information included in the APR alone. Additionally, or in the alternative, the compliance determination may be based on values included within a data field of the APR. For example, if the specified value for a parameter is outside the configured range of the infusion device, the value may be determined to be non-compliant. If the APR is determined to be not compliant, then the request may be rejected and/or cause an error at the device 12. Such errors are indicative of or referred to as misalignment errors.

The foregoing process may be used outside the clinical setting to verify whether medications or parameters therefor stored in the pharmacy information system (e.g., in EMR 202 and/or formulary 204) are misaligned with a drug library deployed in the field. Verification using this process, however, requires a physical infusion device, and typically occurs in the field. Moreover, if a site or care area has multiple pump configurations (e.g., multiple drug library configurations), a verification test may also require different physical infusion devices in each of the configurations, with manual validation of the result at each device. Formularies, however, may include thousands of drug entries, and an incomplete verification of the entries can leave critical, but infrequently used, drugs or device configurations untested. Moreover, automation of the verification process may only be able to determine if the test APR message was accepted by the device, and not how the device actually behaved and/or responded to the message.

Figure 3:
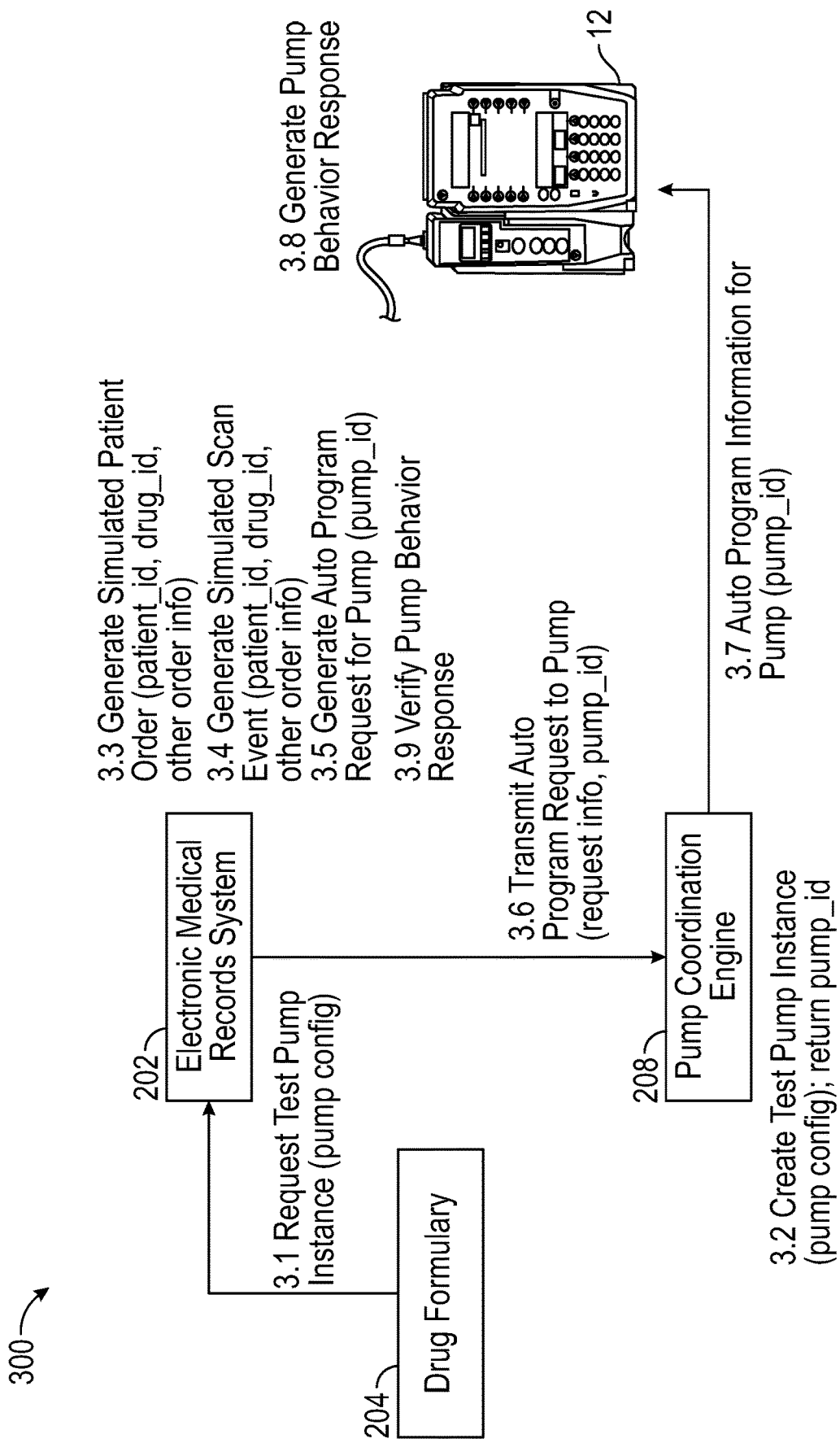
FIG. 3 depicts an example system for scanning and validating clinical order device configurations, according to aspects of the subject technology.

FIG. 3 depicts an example system 300 for scanning and validating clinical order device configurations, according to aspects of the subject technology. In the depicted example, device configurations, including drug libraries, may be scanned and validated by an automated process controlled at the EMR system 202 or via the coordination engine 208. In this regard, the number of test instances, including medical devices, device types, care areas, modules, as well as medication types for each test instance may all be determined by an automated script. The process may be controlled by or at the EMR system or formulary (e.g., at server 30) or by a terminal 32 associated with the system.

In the depicted system, a message requesting a test instance of an infusion device may be first transmitted to the coordination server 208 (3.1). Test instances, as referred to herein, include physical or virtual (described below) medical devices such as infusion devices 12. In the depicted example, the coordination server 208 creates the test instance (3.2) by either locating and/or identifying an existing test instance or activating or creating one virtually. The coordination server then responds to the message request with the test instance. Next, a clinical order setting is identified for each test. The clinical order setting may include runtime parameters including one or more of, for example, pump model (e.g., an identifier for a module of the pump to use for test), pump type (e.g., peristaltic or syringe pump), number of modules, firmware version, drug library, care area, language, whether encryption should be used, and storage location (e.g., ftp or IP address, email, etc.). The clinical order setting may further include runtime parameters particular to the drug library on the test instance, including drug library version, care area, module configuration (e.g., which channel to use on the pump, which may further designate the type of pump used according to the channel), etc. These parameters may be entered by a user at the time of test or may be supplied in a script which is executed for a particular execution cycle. Once the test instance is identified and ready, and the clinical order setting is determined, the EMR system 202 may transmit an APR to the test instance for each of one or more test configurations.

In some implementations, the coordination server 208 may determine the test instance for the EMR 202. For example, the coordination server 208 may receive the request to create the test instance from the EMR, and then identify the test instance based on an included in the request (e.g., from a pool of test instances). In some implementations, the coordination server may query a fleet data store for idle infusion devices corresponding to the identified infusion device type, an identified idle infusion device being returned as the test instance. Once identified, the coordination engine 208 may transmit a response that identifies the test instance to the EMR.

The APR process may function similar to that described with respect to FIG. 2, but in an automated fashion. For example, a patient order may be automatically generated (e.g., by the script), including a patient identifier, drug identifier, and other information pertaining to a clinical order (3.3). The EMR system 202 may further generate a simulated scan event (3.4), such as scanning a medication bar code or QR code at a medical records terminal 206 (see FIG. 2). The simulated scan event further provides the patient identifier, drug identifier, and order information. According to various implementations, a master script may generate scan events, which are then used to query an order database for patient orders. The patient orders may be predetermined or based on actual data.

The EMR system 202 then generates an APR based on each scan event and corresponding order (3.5). The APR may include, for example, a drug identifier and a request to load parameters for a drug corresponding to the drug identifier. In this regard, the APR may instruct the infusion device to load the parameters from an available drug library stored on the infusion device. According to various implementations, the APR may include a concentration for the drug.

The EMR system 202 transmits the APR to the infusion device test instance (3.6). In some implementations, such as that depicted in FIG. 3, the APR is brokered by the coordination server 204, which receives the APR together with a device identifier for the test instance, and then transmits the APR to the test instance to the identifier on behalf of the ERM system 202 (3.7).

The test instance, for example an infusion device 12, receives and processes the APR. The infusion device 12 (and/or processor or system) determines whether the information in the request matches known parameters for the corresponding match in the drug library, and/or whether the APR includes any deviations from information stored on the device (e.g., in the drug library). For example, if the APR includes a certain drug concentration, the infusion device may check the drug library to determine whether the drug concentration received is within an allowable range for the drug identified by the APR. In some implementations, if the drug is not found in the current drug library, the pump is configured to search other drug libraries stored within the pump's memory for the drug. The pump may search based on the name of the drug or based on certain parameters provided in the APR.

When the APR is processed by the infusion device, the infusion device generates a behavior response (3.8), which may include identifying any deviations between the information provided by the APR and the information stored in the device. In some implementations, the test instance identifies a deviation in the received automated programming data with respect to stored programming data. The deviation may arise from a drug identified in the APR not being identified in a currently active first drug library stored in a memory of the test instance. In some implementations, the deviation may include the received concentration of the drug being outside an allowable range for the concentration stored in the drug library for the drug.

In some implementations, a deviation may arise based on the test instance determining that the parameters to be loaded for drug are stored in a deactivated second drug library stored in the memory of the infusion pump. In some implementations, the system may determine that the second drug library is for a different care area than a care area currently activated for the infusion device. In some implementations, the deviation may include receiving an APR for changing a parameter of the infusion of the medication while the infusion is being administered to a patient but determining, when the automated programming data is received, that the infusion is not being administered to the patient.

In some implementations, the test instance includes a first pump channel and a second pump channel (e.g., corresponding to multiple infusion modules 18, 20). The system may identify the first pump channel for receiving the automated programming data and determine that the parameters to be loaded are more aligned with the second pump channel than with the first pump channel. In some implementations, the deviation may include the automated programming data being for a drug to be administered after a first drug is administered to the patient, but the first drug is not currently being administered.

If no misalignment error was produced (e.g., the parameters were accepted and congruent with the drug library on the device), the infusion device may send confirmation to the EMR system 202 (e.g., via coordination engine) that the APR message was accepted and processed (e.g., understood). If a parameter (such as the concentration or other parameter) is outside of an allowable range (e.g., clinically defined dose error reduction range), then the system may return a misalignment error.

According to various implementations, the response to the APR from the test instance (3.8) may include information pertaining to the results of the internal processing of the APR by the test instance, in addition to confirmatory information. The response may be in the form of one or more messages, including a transaction identifier (corresponding to the identifier received by the test instance), a message type (e.g., an acknowledgement message or error message), the device identifier for the test instance, a time stamp associated with the receipt and processing of the APR, and a message payload. In some implementations, the APR response may include a test response flag (e.g., a field identifying that the response is a test and not a real patient order; that the EMR is not to take official action on the response). Optionally, echo test data may be included that was submitted when the test instance was created. Such data allows the testing system to include its own metadata to facilitate an automated review of the responses. The echo test data may be returned as provided. In some implementations, the echo test data may include some substitution fields (e.g., device ID, time stamp, etc.) to allow custom field formatting for echo responses.

In some implementations, the test instance may include screen capture data, for example, in the form of images indicative of each step associated with programming the test instance based on the received APR. In an infusion device that is not configured to be fully automated, such screen captures may obtained as a clinician steps through a manual programming process, for example, by clicking next on each screen. Some infusion devices may operate in a fully automated test mode wherein the test instance will simulate clicking "next" until the option of "start" is offered, each screen being captured and encoded (e.g., as a binary image) and appended to the APR message response that is sent to the EMR system 202. In some implementations, the APR response may include a user interface step-through, which may be stored by the EMR system 202 (e.g., in a database 37) and recalled to review when diagnosing the cause of misalignment errors. As will be described further, the test instance may (additionally or in the alternative) run in a "virtual mode" by which all processing is performed by software in a simulation environment.

The programming response received from the infusion device is stored in a database 37 associated with the records system. In this regard, the records system (or a user accessing the records system) may access the data to verify pump behavior (3.9), as needed.

Figure 4:
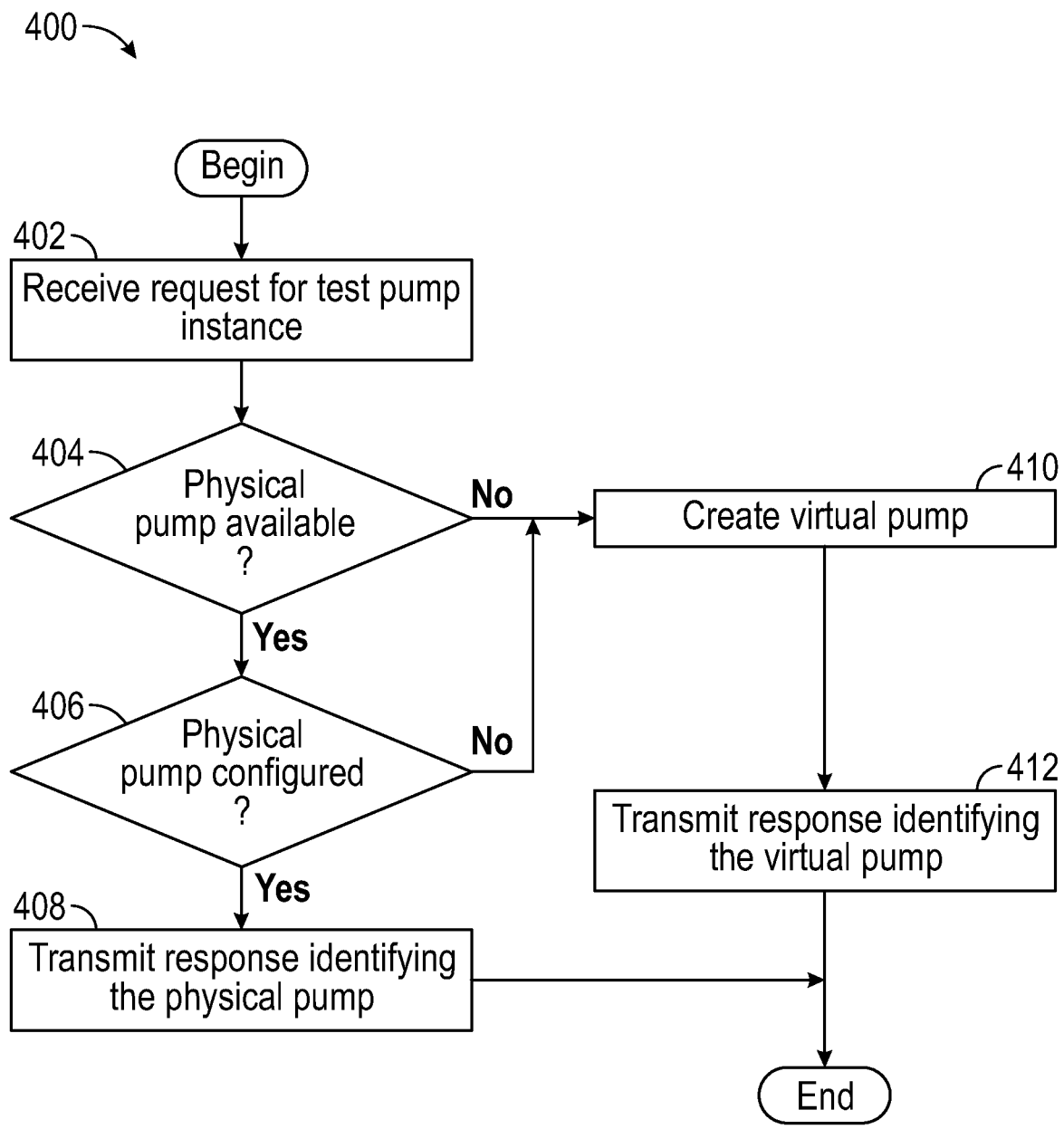
FIG. 4 depicts a first example process for establishing a virtual test instance for automated scanning and validating clinical order device configurations, according to aspects of the subject technology.

FIG. 4 depicts a first example process 400 for establishing a virtual test instance for automated scanning and validating clinical order device configurations, according to aspects of the subject technology. For explanatory purposes, the various blocks of example process 400 are described herein with reference to FIGS. 1A, 1B, 1C, and 2, and the associated components and/or processes described herein. The one or more of the blocks of process 400 may be implemented, for example, by one or more computing devices including, for example, server 30 and/or medical device 12. In some implementations, one or more of the blocks may be implemented based on one or more machine learning algorithms. In some implementations, one or more of the blocks may be implemented apart from other blocks, and by one or more different processors or devices. Further, for explanatory purposes, to the extent that the blocks of example process 400 are described as occurring in serial, or linearly, in some implementations, multiple blocks of example process 400 may occur in parallel. In addition, the blocks of example process 400 need not be performed in the order shown and/or one or more of the blocks of example process 400 need not be performed.

In the depicted example, a request for a test pump instance is received by a server (402). In some implementations, the server may include one or more components of a pharmacy information system, including the EMR system 202 and/or a formulary 204. In some implementations, the server includes the coordination engine 208. In the depicted example, the server (e.g., the coordination engine 208) receives the request and first determines whether a physical infusion device 12 is available (404). For example, the server may maintain or access a fleet data store of infusion devices within the hospital's network. The data store may be continuously updated to identify which of the infusion devices are currently active (e.g., registered on the network and able to receive communications). In this regard, the server 208 may query the fleet data store for an idle infusion device corresponding to the infusion device identified in the request (e.g., including pump model, modules, firmware version, drug library, care area, etc.).

When an idle pump is available (e.g., not in use with a patient), the server may determine whether the pump includes a configuration that matches the data of the request (406). If the pump is available and is configured according to the requested infusion device, then the pump is reserved for the instant scanning and validation procedure. In this regard, server may lock the pump for use by server, preventing it from being used with a patient in a clinical setting until the scanning and validation process is completed. The server may then transmit a response identifying the physical pump to the requestor (e.g., requesting server) (408).

If a physical pump is not found to be idle or otherwise available, or if an available pump is not found to be compatible with identified data, then the coordination server 208 may create a virtual instance of the pump (410). In this regard, the coordination engine 208 may include a software development sandbox in which virtual instances of infusion devices may be modeled and interacted with as if they were real physical devices. The virtual instance may be capable of executing the same or similar software utilized by the corresponding physical device (e.g., in a contained virtual environment), and generate graphical images of its physical user interface as if a user were viewing the physical device, including programmatic readouts and operational parameter values. For software utilized by infusion devices that provide graphical displays of their entire user interface, each display may be captured and returned to the calling server as part of a response.

A virtual instance may extend (e.g., via the sandbox) a virtual communication interface for communicating with remote systems using a message protocol similar or identical to the physical infusion device which it models. In this manner, the virtual instance is capable of receiving and processing APRs and receives and processes automated programming commands from the server in the same manner as a physical infusion device. The APR may be sent by the EMR system 202 to the virtual instance (e.g., via the coordination server 208) and instruct the virtual instance regarding an infusion of a medication.

On identification of the virtual instance, the server (e.g., the coordination engine 208) transmits a response to the pharmacy information system (e.g., the EMR system 202) identifying the test virtual instance (412). The server (e.g., the coordination engine 208) may create multiple instances, each with different clinical data settings and configurations. For example, a script may identify a plurality of infusion devices, which may then be either identified in a physical environment or created virtually, as previously described.

Figure 5A:
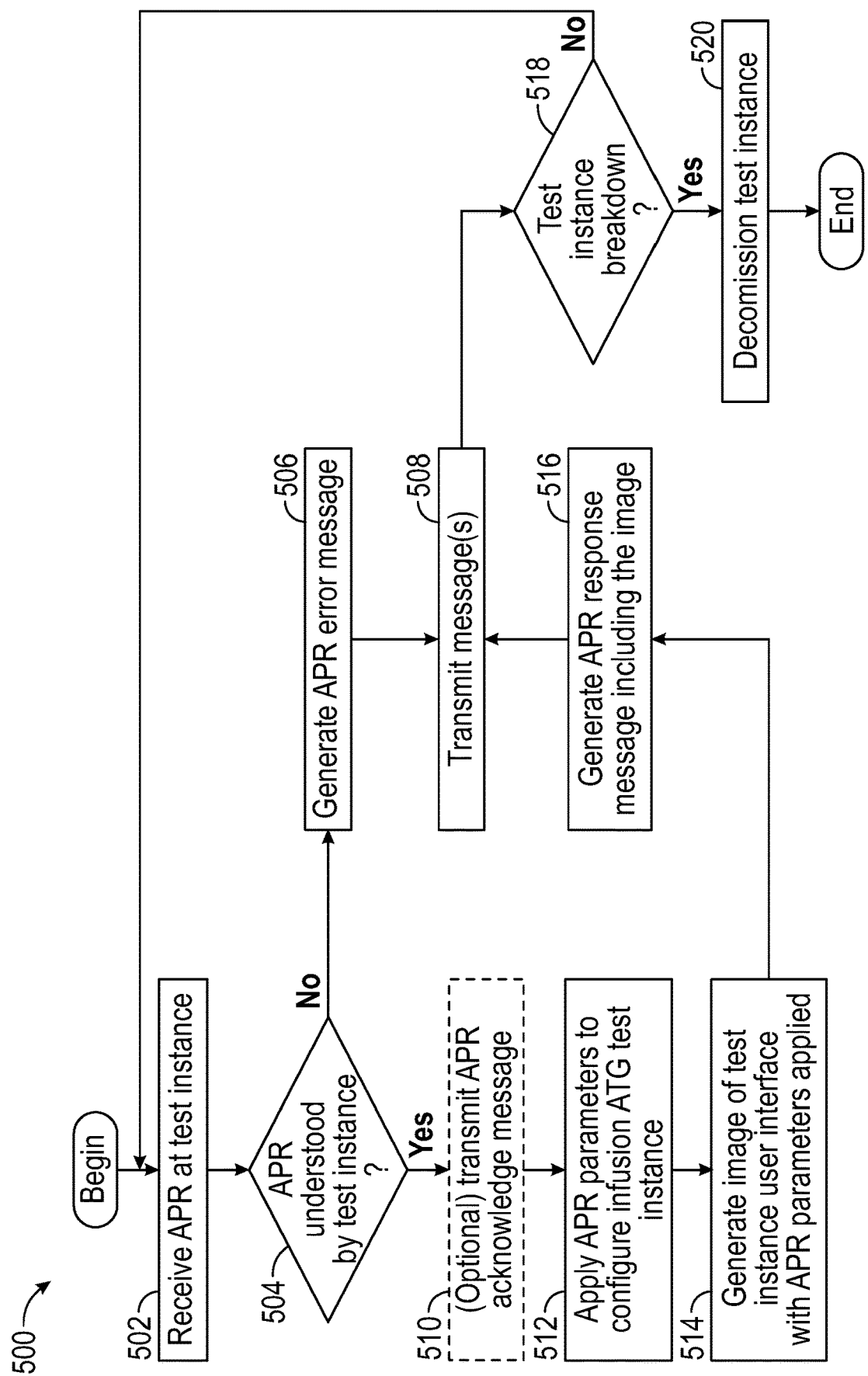
FIG. 5A depicts an example process for remote automated scanning and validating clinical order device configurations, according to aspects of the subject technology.

FIG. 5A depicts a first example process 500 for remote automated scanning and validating clinical order device configurations, according to aspects of the subject technology. For explanatory purposes, the various blocks of example process 500 are described herein with reference to FIGS. 1A, 1B, 1C, 2, 3, and 4 and the associated components and/or processes described herein. The one or more of the blocks of process 500 may be implemented, for example, by one or more computing devices including, for example, server 30 and/or medical device 12. In some implementations, one or more of the blocks may be implemented based on one or more machine learning algorithms. In some implementations, one or more of the blocks may be implemented apart from other blocks, and by one or more different processors or devices. Further, for explanatory purposes, to the extent that the blocks of example process 500 are described as occurring in serial, or linearly, in some implementations, multiple blocks of example process 500 may occur in parallel. In addition, the blocks of example process 500 need not be performed in the order shown and/or one or more of the blocks of example process 500 need not be performed.

As described previously, a request for a test instance of an infusion device is received, and the test instance is created and identified based on the request. A server then sends, or causes to be sent, an automated programming request (APR) to be transmitted to the identified test instance, including validation information for validating clinical order data. The depicted example describes how the test instance handles the request.

In the depicted example, the APR is received at the test instance (502). In the case of a physical test instance (e.g., an idle infusion device) connected to a hospital network 10, the APR is received over the network using the device's network communication interface 52. When the test instance is a virtual instance, the virtual instance extends a virtual communication interface for communicating with the server using a message protocol identical to the physical infusion device. In this regard, automated programming commands are received and processed in a normal manner to instruct the test instance.

The test instance receives and begins processing of the APR. In this regard, the test instance (and/or processor or system) determines whether the APR and its content are compliant (504). The compliance determination may be based on the data fields included in the APR (e.g., in the validation information). For example, the test instance determines whether the information in the APR corresponds to a drug library loaded into memory of the test instance, and/or whether the information is congruent with or an acceptable match with information of the drug library, or whether there any deviations between the information stored on the device (e.g., in the drug library) and the information provided in the APR. For example, the APR may include or omit a field that may prevent the pump from parsing or auto-programming the pump using the order alone. If an expected field is omitted then the APR may be determined to not be compliant. The compliance determination may be based on values included within the data fields of the APR. For example, if the specified value for a parameter is outside the configured range of the infusion pump, the value may be determined to be non-compliant. If the APR includes a certain drug concentration, the infusion device may check the drug library to determine whether the drug concentration received is within an allowable range for the drug identified by the APR. In some implementations, if the drug is not found in the current drug library, the pump is configured to search other drug libraries stored within the pump's memory for the drug. The pump may search based on the name of the drug or based on certain parameters provided in the APR. Determining whether the request is compliant may also include determining whether it is compliant with a protocol understandable by the test instance.

If the information of the APR (such as, e.g., a drug concentration or other parameter) is outside of an allowable range (e.g., clinically defined limits/guiderails), or the APR itself is malformed (e.g., missing a field), or a requested drug library is unavailable, or the APR is otherwise non-compliant then the system may generate an error message (506), indicating a misalignment between the APR and the information stored within the test instance (e.g., within a drug library). A misalignment error may also be returned if a parameter (such as the concentration or other parameter) is outside of an allowable range (e.g., clinically defined dose error reduction range). The error message may then be transmitted to the server 30 (508) or may be queued for transmission with other messages.

If the APR is (at least initially) understood then the test instance may (optionally) send an acknowledgement back to the server (510), indicating that the APR was compliant and that the APR will be processed by the test instance. The test instance then, responsive to or after determining that the APR is compliant, may proceed to configure itself according to the information received in the APR (512). In this regard, the APR may identify a medication, and the test instance may determine that a drug library loaded into the test instance includes the medication. The test instance may then set the operational parameters of the test instance based on the parameters in the drug library corresponding to the medication. In this regard, the test instance (whether physical or virtual) configures itself to deliver the medication to a patient using the parameters associated with (or indexed by) the information identified in the APR.

If no error was produced (e.g., the parameters were accepted and congruent with the drug library on the device), the test instance generates a response for transmission to the originating requesting service (e.g., the EMR system 202 or formulary 204). As part of the response, the test instance may generate one or more images (e.g., screenshots) of a graphical user interface that would be presented by the infusion device configured according to the automated programming command (514). As described previously, the APR response may include a user interface step-through, represented by a series of images illustrative of what the user interface of a physical infusion device would display during acceptance and configuration of the parameters loaded in response to the APR. In this regard, any errors that would be apparent by way of the user interface may be captured and transmitted in the response for a subsequent evaluation of any misalignment errors.

The test instance, the server hosting the test instance, or the server responsible for communication with the test instance (e.g., the coordination engine 208) generates the response message including the one or more images (516). In addition to any images, as described previously, the response to the APR from the test instance may include information pertaining to the results of the internal processing of the APR by the test instance, in addition to confirmatory information. The response may be in the form of one or more messages, including a transaction identifier (corresponding to the identifier received by the test instance), a message type (e.g., an acknowledgement message or error message), the device identifier for the test instance, a time stamp associated with the receipt and processing of the APR, and a message payload (which may include the images in binary form). Once the response is generated, the response may be transmitted back to the requestor (508).

After a response to the APR is generated and transmitted, the test instance, or the server responsible for its creation or identification (e.g., an EMR server or coordination engine server) determines whether the test instance should be decommissioned; for example, broken down, deleted, terminated, deprecated and/or removed from memory (518). In some implementations, the test instance or the server responsible for causing its creation waits until it specifically receives an instruction to decommission the test instance. In some implementations, multiple APRs are intended for a single test instance, and the test instance or the server may wait until all APRs are received and processed before the test instance is decommissioned. In some implementations, the server responsible for causing creation of, or initiating, the test instance may provide an indication to the test instance of how many APRs are to be sent, or that there will be multiple APRs (or a single APR) before the test instance should be decommissioned. Additionally, or in the alternative, each APR may indicate its sequence number with respect to other APRs designated for the test instance. When the last sequence number is reached, the test instance may be decommissioned (520). If an APR (or the first instruction) indicates that more APRs are expected, then the test instance may wait to receive the next APR (502).

Figure 5B:
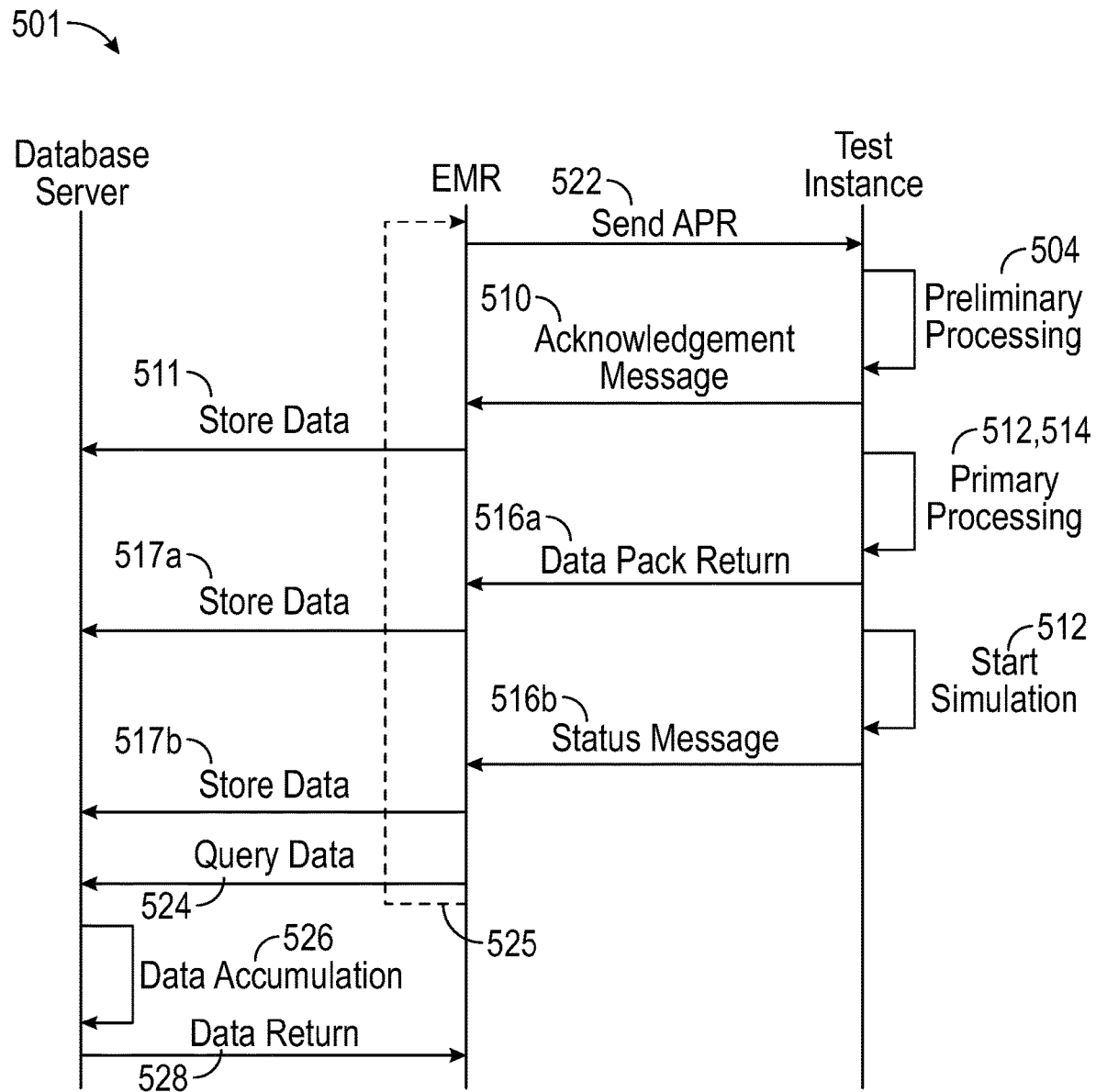
FIG. 5B depicts an example process flow for remote automated scanning and validating clinical order device configurations, according to aspects of the subject technology.

FIG. 5B depicts an example process flow 501 for remote automated scanning and validating clinical order device configurations, according to aspects of the subject technology. For explanatory purposes, the various blocks of example process flow 501 are described herein with reference to FIG. 5A, and in further reference to FIGS. 1A, 1B, 1C, 2, 3, and 4 and the associated components and/or processes described herein.

As described previously, a request for a test instance of an infusion device is received, and the test instance is created and identified based on the request. A server then sends, or causes to be sent, an automated programming request (APR) to be transmitted to the identified test instance (522). According to various implementations, the APR may include information for programming an infusion device according to a patient order. In this regard, the order may include or be associated with an identifier and/or name for the drug, a volume to be infused, drug amount or concentration, dosage units, diluent volume, and other parameters. According to various implementations, some or all of this information is provided as validation information for validating clinical order data.

As described previously, the APR is received at the test instance and preliminary processing (504) is performed by the test instance to determine whether the APR and content of the APR are compliant. The compliance determination may be based on the format of the APR, data fields included in the APR, and/or the parameters provided within the APR message(s). For example, an APR may fail compliance because it includes or omits a field that may prevent the test instance from parsing or auto-programming the test instance using the APR or order identified by the APR. In another example, if the specified value for a parameter is outside the configured range of the (simulated) infusion pump, the value may be determined to be non-compliant. If not compliant with the protocol, then the request may be rejected in part because the test instance cannot process the request. If the APR is compliant with an understandable protocol, then the APR may then be accepted, and an acknowledgement may be sent (510) from the test instance to the EMR system 202 (e.g., via coordination server 208) indicating that the APR is being processed.

If the APR is (at least initially) understood then the test instance may (optionally) send an acknowledgement back to the server (510), indicating that the APR was compliant and that the APR will be processed by the test instance. The acknowledgement message may indicate whether the message was well formatted (e.g., all fields present, valid, etc.), and/or whether the request parameters and/or limits were accepted. The acknowledgement message may include information within a drug library on the (simulated) pump that corresponds to the APR or the information provided with the APR. For example, the acknowledgement may provide an alias for the drug identified in the APR or the order identified by the APR. Some example message fields and values that may be included in the acknowledgement are further described in Table 1.

TABLE 1

APR Acknowledgement Message

| | |
|---|---|
| a. | Message well formatted |
| | i. All required fields present |
| | ii. All fields valid |
| b. | Request parameters with limits |
| | i. System |
| | ii. Care area |
| c. | Infusate information in drug library |
| | i. Alias or drug identifier |
| | ii. Drug amount |
| | iii. Diluent volume |
| | iv. Dosage units |
| d. | Inappropriate pump state for APR type; |
| | APR types include, e.g., initial, secondary, subsequent, titrate, bolus, flush |

On receipt of the acknowledgement message(s) the EMR system may then store the data (511) in a database 37. In this manner, all of the data for the test may be collected by the database for later retrieval and analysis to determine the degree of misalignment between the EMR and/or formulary systems and drug libraries deployed into a hospital organization (e.g., as simulated by the test instances). In some implementations, the acknowledgment message(s) may not include data that can be stored, or the message(s) may not be sent or stored at all. In such implementations, the test instance may begin primary processing (512, 514), as described with regard to FIG. 5A, and the information may be returned with the data returned in the APR response message (516*a*) as described with regard to FIG. 5A. The returned data may include, for example, user interface screenshots and workflow fields and values that would be presented by an actual infusion device during automated programming based on the received APR. The data and captured screenshots returned in the APR response message may then be stored (517*a*) in the database 37 for further analysis. Some example message fields and values that may be included in the APR response message 516 are further described in Table 2.

TABLE 2

Infusion Device Workflow Message(s)

| | |
|---|---|
| a. | Infusate appears as expected |
| b. | Error Messaging for APR |
| c. | Pump State |
| d. | Limits violations |
| | i. Disposables |
| |    1. Volume to be infused (VTBI) exceeds avail volume. |
| |    2. Rate exceeds disposable type |
| | ii. Guardrails |
| |    1. Soft |
| |    2. Hard |
| e. | Clinical Advisories |
| f. | Medication Contraindication |
| | i. Based on lab values |
| | ii. Allergy Checks |
| | iii. Drug to drug interaction |
| g. | Therapy selection |
| h. | Other Notifications |
| | i. Rate Change to program |
| i. | Page to page transition workflow |
| | i. Loading/unloading containers |
| j. | Any additional fields requiring population |

The data fields and values returned with the APR response may be based on calculations undertaken by the simulated infusion device (e.g., by the test instance). Such calculations may be performed without human involvement. Certain values may be calculated based on values sent in the APR. For example, BSA (body surface area) may be calculated based on a weight provided in the APR, or based on a lookup of the patient's weight based on a patient identifier included in the APR. The test instance simulation may automatically accept all available user acceptance options, as if a user reviewed the data provided by the APR and/or the calculations based on the APR at the device, and accepted the programming (e.g., without change). In some implementations, a calculation performed by the test instance may cause a termination of the programming, and the test instance will report the reason for failure and include a copy of all information leading up to the failure in the APR response message (516). For example, a VTBI may be calculated based on a provided concentration and weight of the patient, and the VTBI may exceed an available volume. Accordingly, the test instance may terminate the infusion and report the error along with the calculated parameters, as described previously and further below. The APR response message (516) may also indicate precision misalignments. For example, the message may indicate that the simulated infusion device accepted one decimal point precision when four decimal points were provided (or vice versa), or accepted a subset of a character string (e.g., 16 of 18 characters of the patient identifier). It is noteworthy that some or all of these calculations may be performed during preliminary processing (504) and the misalignments (including, e.g., captured screenshots corresponding to the calculated data) reported in the acknowledgement message (510).

After the APR has been accepted and processed (512, 514) by an infusion device without failure, the infusion device will start and begin to infuse a medication according to the programming provided by the APR. After the infusion has begun, the infusion device will send one or more status messages to the EMR system 202. A status message informs the EMR system what was started and includes certain values on which the infusion device is reporting. This information may reflect the APR data and/or may include changes made at the device. The EMR system may wait for the status message and, upon receiving the message, closes out the workflow pertaining to the APR.

According to various aspects of the subject technology, as the test instance simulates a live infusion device, the test instance will simulate the start of an infusion (512) and then provide one or more status messages back to the EMR system 202 (516b). When the simulation starts, the test instance will perform further calculations based on data that it has been provided, either by the APR or by information obtained by the test instance based on the APR (e.g., based on patient or order information, or information from a drug library). The EMR system may monitor the test instance to close out the APR simulation test.

On receiving the status message(s), the EMR system may store (517b) the data therein in the database 37, together with the previously received data, for further analysis. Some example message fields and values that may be included in the one or more status messages provided by the test instance are further described in Table 3.

TABLE 3

Infusion Status Message(s)

| | |
|---|---|
| a. | Value Alignment |
| | i. Flow rate |
| | ii. Volume to be infused |
| | iii. Dose |
| | iv. Volume Accumulation over time |
| b. | Value Check |
| | i. Order ID |
| | ii. Patient Info |
| |    1. ID or identifier |
| |    2. Weight |
| |    3. BSA |
| | iii. Clinician ID |
| | iv. Infusate Info |
| |    1. Alias or Drug Identifier |
| |    2. Drug Amt |
| |    3. Diluent Vol |
| |    4. Dosing Units |
| c. | Expected start and completion event relative to time |
| d. | Cancel programming |

Each message received from (or sent to) the test instance may include a unique identifier that was, for example, provided with the original APR. In this regard, all of the stored data, together with the APR, may be stored in the database for collective retrieval. After storing the status message data, the EMR may close the current APR test. If there are more data groups identified for testing (and/or APRs) then the EMR system may repeat (525) the process of FIG. 5B for each data group to be tested. In this regard, multiple APRs may be initiated by a script to test a library of medications in a formulary against drug libraries deployed in the field, or to test whether the drug libraries are suitable for deployment in the field such that their data field conform with expected data fields based on known formulary information.

An administrator may then query (524) the test data (e.g., from a terminal 32) to obtain test results. The EMR system 202 maintains log files for each test in database 37, indexed by the previously described unique identifier. When the query is received, all the data for the identifier may be accumulated (526) and processed to determine misalignments for a particular test, and returned (528) to the user. In some instances, a misalignment may have been identified by the test instance and included in the data returned to the EMR system. In some instances, misalignments are identified by comparing data returned from the test instance (e.g., from the acknowledgement, APR response message, and/or status message) with data in the EMR system or formulary information. As described previously screenshots (e.g., images) of a (simulated) physical infusion device interface are captured and stored with the data, and provided to the user to accurately depict how an infusion device reacted to a misalignment.

FIGS. 6A, 6B, and 6C depict a series of user interfaces 602, 604, 606, in an example infusion programming workflow for automated programming an infusion device, according to various aspects of the subject technology. The depicted screens 600 may be displayed on a display 6a of a control unit 14. The depicted example screens are displayed to facilitate selection of a parameters automatically populated responsive to an automated programing request (APR).

When an APR is received a processed by an infusion device, and no misalignment errors are received, the infusion device will display (e.g., on display 6a) a series of programming confirmation displays in a predetermined workflow. In this manner, a clinician—instead of having to enter parameters manually—may merely review the parameters populated into the designated fields by way of the APR. For example, the APR may cause a drug library on the device to load the drug amount, diluent volume, and dosage units from a drug library stored on the device. In some instances, wherein the APR includes patient information (e.g., a patient identifier), patient parameters such as patient weight may also be loaded and displayed. As depicted, there may be multiple screens of confirmation.

According to various implementations, the graphical user interface screens may be captured for each step of the program associated with the APR. When a physical device is used as the test instance and/or manual confirmation is required, the test instance may capture each screen as it is confirmed by a clinician. In automated implementations, the test instance may simulate clicking "next" (e.g., FIG. 6A) until the option of "start" is offered (e.g., FIG. 6B). The test instance may then simulate a start of the infusion and a final image (e.g., FIG. 6C) may be captured. The captured images may then be appended to the APR response and returned to the requesting system, as previously described.

FIG. 6D depicts an example user interface 608 in which an automated programming request resulted in an error, according to various aspects of the subject technology. If an APR is well formed an acknowledgement may be sent to the requesting system to indicate that the message was understood. However, as depicted in this example, data included in the APR may violate an institutional rule. In such instances, the test instance may capture an image of the user interface displaying the error and include the image in the response sent to the requesting system (e.g., at the end of the images). In some cases, one screen may be approved (e.g., FIG. 6A), but a subsequent step may include a violating value. In that case, image(s) of the UI prior to the error may be included in the response transmitted by the test instance. The system may simulate acceptance of the error so that all the screens are captured to completion of the APR programming.

According to various implementations, as described previously, multiple APRs may be initiated by a script. The requesting system (e.g., the coordination engine 208) may maintain and provide for display a log file of the results from one or more of the test instances. Each log file may include a list of all the APRs transmitted, further identified as either passing or failing. Each log file may be provided to a client device as a user interface of results (e.g., a webpage formatted in HTML), and include with each entry one or more hyperlinks which, when selected, provides further information about the entry. For example, a user may be able to view the user interface, select a hyperlink corresponding to the images associated with the respective APR, and step through the images. In this manner, a user may view the images generated in response to each respective APR for each respective test instance.

The user interface may be sortable to display a list of all APR failures, or a list of failures by category (e.g., pump model, type, drug library version, care area, etc.). A user may then select which entry to further review and obtain a visual of the infusion device during processing of the APR, thereby identifying the failures visually as needed. In some implementations, the system may provide one or more hyperlinks connected to entries within the drug library to make corrections. For example, the drug libraries may be stored in a central database 37 and downloaded as needed or deployed to physical devices. A clinician (e.g., working from a terminal 32) may select a hyperlink corresponding to a failure, and select a corresponding hyperlink to access an editable input field to view and/or modify the corresponding value(s) within the database. The drug library associated with the entry may then be updated and designated (e.g., by the user) for deployment to corresponding devices employing the library via the network 10 at a schedule time.

Figure 7:
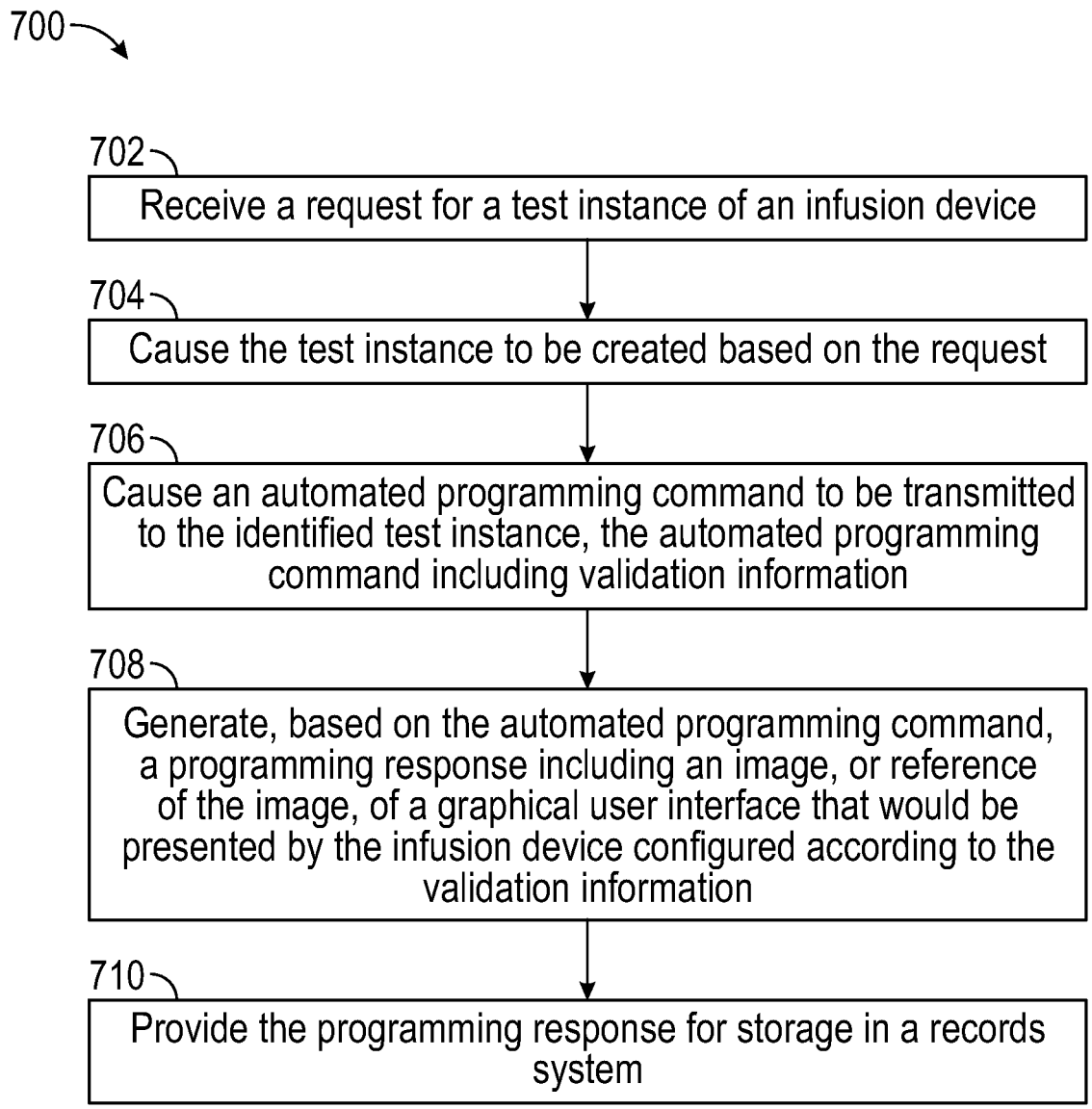
FIG. 7 depicts an example process for remote automated scanning and validating clinical order device configurations, according to aspects of the subject technology.

FIG. 7 depicts an example process 700 for remote automated scanning and validating clinical order device configurations, according to aspects of the subject technology. For explanatory purposes, the various blocks of example process 700 are described herein with reference to FIGS. 1A, 1B, 1C, and 2 through 6 and the associated components and/or processes described herein. The one or more of the blocks of process 700 may be implemented, for example, by one or more computing devices including, for example, server 30 and/or medical device 12. In some implementations, one or more of the blocks may be implemented based on one or more machine learning algorithms. In some implementations, one or more of the blocks may be implemented apart from other blocks, and by one or more different processors or devices. Further, for explanatory purposes, to the extent that the blocks of example process 700 are described as occurring in serial, or linearly, in some implementations, multiple blocks of example process 700 may occur in parallel. In addition, the blocks of example process 700 need not be performed in the order shown and/or one or more of the blocks of example process 700 need not be performed.

In the depicted example, a request for a test instance of an infusion device is received (702). The request for the test instance may originate from a pharmacy information system to determine whether drug information stored in a formulary is consistent with drug information stored in one or more drug libraries configured for use by infusion devices in a hospital network (e.g., in drug libraries currently deployed or designated for deployment to the infusion devices). The pharmacy information system may include a records system such as the formulary 204 and/or an EMR system 202. The request may be initiated by a user, or by an automated script. For example, a script may be created and executed to procure known types of infusion devices capable of storing drug libraries designated for validation.

With further reference to FIG. 7, the requested test instance is caused to be created and identified based on the request (704). According to some implementations, the request includes test instance identification information for identifying and creating the test instance within a physical operating environment. A server receiving the identification information (e.g., a server 30 including the coordination engine 208) creates and/or maintains a pathway for communication with the test instance. For example, the server may query a fleet data store (e.g., in database 37) for an idle infusion device corresponding to the infusion device identified in the request (e.g., identified by type, model, capabilities, etc.). If an idle infusion device matching the description is identified within the hospital network, the device may be reserved for validating formulary information via one or more APR commands sent from the pharmacy information system to the test instance. In this regard, the identified idle device may be locked for use as the test instance, preventing its use a patient until it is released after the procedure.

In some implementations, the pharmacy information system confirms the availability of the infusion device with the infusion device. For example, the server may discover the device in the fleet data store, and then query the device location on the network 10 using the device's identifier and confirm the device is still idle. Once an idle device is confirmed, the server may create an interface for communicating with the infusion device and provide an identifier of the test instance to the pharmacy information system. In this regard, the server may extend a virtual interface for the device so that a requesting server within the pharmacy information system may communicate with the device, including sending the device an APR and receiving a response.

If a device is not available, for example, a device is not idle in the fleet data store or its availability cannot be confirmed, the server may cause the instantiation of a virtual instance of an infusion device as the test instance based at least in part on the request. In some implementations, a virtual instance will be created without the need for first determine whether an idle physical device exists. In some implementations, a server may generate multiple virtual instances, and the fleet data store may be used to identify idle virtual instances. The virtual instance may be locked until it is released after the procedure so that other servers are prevented from using it.

Each virtual instance may extend a virtual communication interface for communicating with remote systems using a message protocol of the infusion device, and for receiving and processing automated programming commands (or APRs) that instruct configuration of infusion devices regarding an infusion of a medication (e.g., according to drug libraries stored on the devices). In other words, a virtual instance may include software that behaves like a physical infusion device. In some implementations, a virtual instance may execute the same software that is executed in a corresponding physical device. The pharmacy information system alone or via the coordination engine may communicate with the virtual instance using the virtual communication instance just as if it was communicating with a real physical device of the same designation (e.g., infusion device type, model, version, etc.).

After the test instance is confirmed to be available or is generated virtually, an automated programming command (or APR) is transmitted to the identified test instance (706). In some implementations, the APR is transmitted by the records system. The APR may be received by a coordination engine 208 before it is transmitted to the identified test instance, and the coordination engine 208 may coordinate communication between the records system and the test instance.

The automated programming command may include validation information for validating clinical order data. The clinical order data may correspond to data stored in the formulary 204, and/or in a drug library configured for the requested infusion device. The purpose of providing the validation information to the test instance is to determine whether the data in the formulary and in the drug library are aligned with each other. In this regard, the validation information may directly correspond to information within the formulary and may be sent to the test instance for the purpose of validating the clinical order data stored in the drug library.

In some implementations, the validation information may identify specific drug library information stored in a drug library configured for deployment by the infusion device. For example, drug libraries may be stored in a database 37 and deployed periodically to infusion devices. The validation information may include and/or identify information in the formulary 204 that is also expected to be in a respective drug library. Once received by the test instance, the APR (and validation information) causes the test instance to be configured by identified drug library information from a drug library deployed to the test instance. If the validation information sent with the APR matches the drug library information then the configuration will pass. Otherwise, as described previously, the configuration may result in a misalignment error.

Based on the automated programming command being transmitted to the test instance, a programming response is generated (708). The programming response includes information pertaining to how the test instance reacted or performed based on the APR. As described previously, the programming response may include an image, or reference of the image, of a graphical user interface that would be presented by the infusion device configured according to the automated programming command. According to various implementations, the programming response identifies one or more deviations between the validation information (e.g., based on formulary information) and the drug library information.

In some implementations, a test instance may receive the programming response and generate graphical user interface images based on the infusion device software running on the test instance. In this regard, the test instance has no control over how the APR is processed. In the case of a virtual instance, the APR is processed just as it would be had it been sent to a physical device executing the same software. Accordingly, in some implementations, the test instance or the coordination server may receive the images and extract text from the images using optical character recognition, and then compare the extracted text with expected test for a clinical order associated with the APR. Based on this comparison, a misalignment error may be identified and the programming response may be updated with the misalignment error together with an identification of the field associated with the error. In some implementations, the images may be compared to reference images associated with the clinical order, and the comparison may determine whether the images correspond to the reference images. As described previously, the programming response may be updated to include a walk-through of multiple screens, recreating an infusion device user interface as it would have appeared had a user reviewing the response been at the device when it received the APR.

After the programming response is generated, the programming response is provided to the records system for storage (710). The response may be provided to the EMR system 202 by the coordination engine 208. In implementations wherein the coordination engine is omitted, the response may be directly provided to the EMR system 202. In some implementations, the response may be stored separately from any images provided with the response. In this regard, the response may include a reference (e.g., a hyperlink) to each image. The responses may be stored in a first database and the images may be stored in a second database. When the records are retrieved from the first database and displayed for review, a user may use the hyperlink to pull the images from the second database.

Many of the above-described example processes 400, 500, and 700 and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, any combination of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 8:
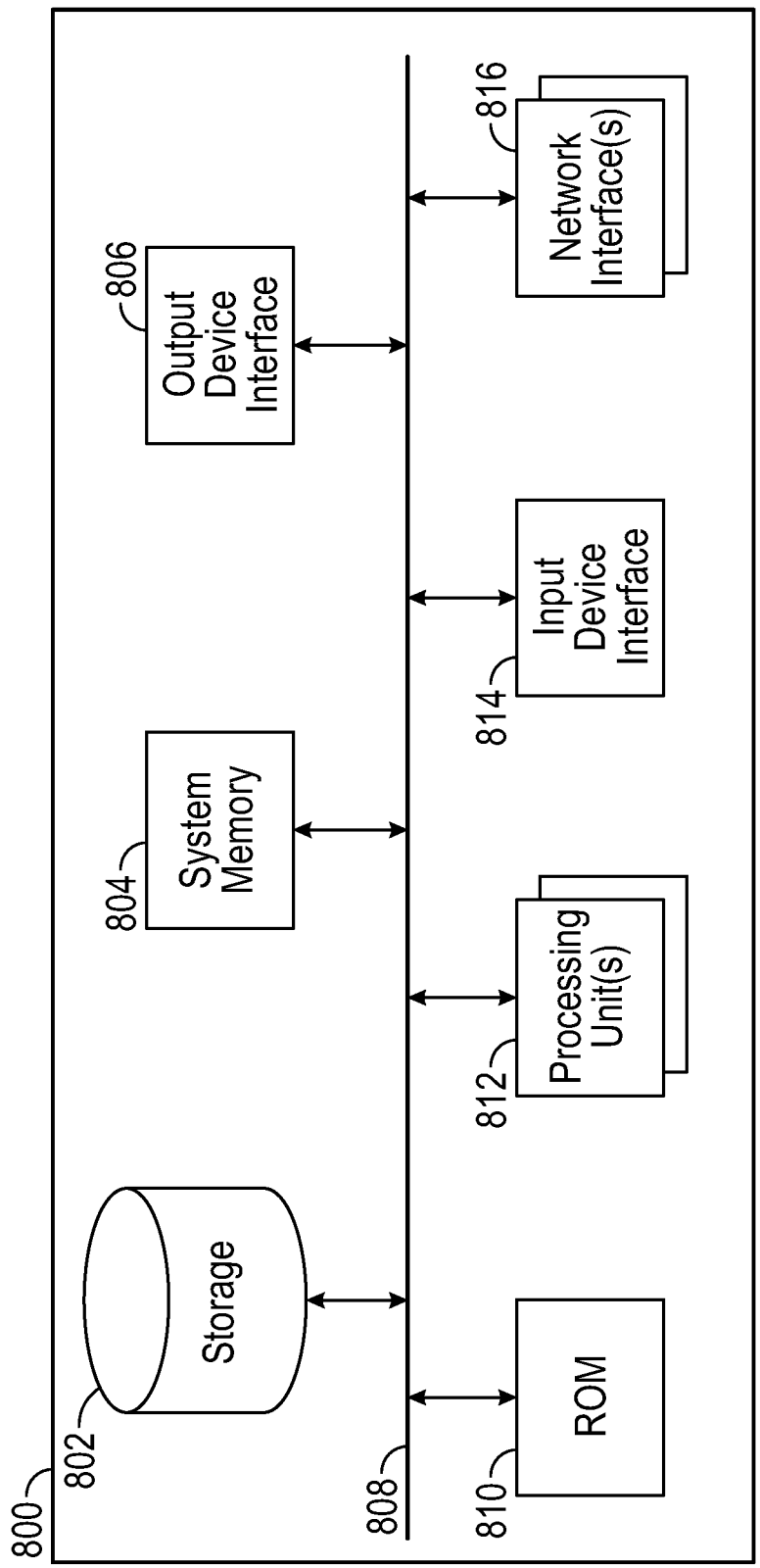
FIG. 8 is a conceptual diagram illustrating an example electronic system for automated scanning and validating clinical order device configurations, according to aspects of the subject technology.

FIG. 8 is a conceptual diagram illustrating an example electronic system 800 for automated scanning and validating clinical order device configurations, according to aspects of the subject technology. Electronic system 800 may be a computing device for execution of software associated with one or more portions or steps of processes 400, 500, and 700 or components and methods provided by FIGS. 1-7, including but not limited to computing hardware within server 30, terminal 32, or patient care device 12, and/or any computing devices or associated terminals disclosed herein. In this regard, electronic system 800 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or any other sort of computer-related electronic device having network connectivity.

Electronic system 800 may include various types of computer readable media and interfaces for various other types of computer readable media. In the depicted example, electronic system 800 includes a bus 808, processing unit(s) 812, a system memory 804, a read-only memory (ROM) 810, a permanent storage device 802, an input device interface 814, an output device interface 806, and one or more network interfaces 816. In some implementations, electronic system 800 may include or be integrated with other computing devices or circuitry for operation of the various components and methods previously described.

Bus 808 collectively represents all system, peripheral, and chipset buses that communicatively connect the numerous internal devices of electronic system 800. For instance, bus 808 communicatively connects processing unit(s) 812 with ROM 810, system memory 804, and permanent storage device 802.

From these various memory units, processing unit(s) 812 retrieves instructions to execute and data to process, in order to execute the processes of the subject disclosure. The processing unit(s) can be a single processor or a multi-core processor in different implementations.

ROM 810 stores static data and instructions that are needed by processing unit(s) 812 and other modules of the electronic system. Permanent storage device 802, on the other hand, is a read-and-write memory device. This device is a non-volatile memory unit that stores instructions and data even when electronic system 800 is off. Some implementations of the subject disclosure use a mass-storage device (such as a magnetic or optical disk and its corresponding disk drive) as permanent storage device 802.

Other implementations use a removable storage device (such as a floppy disk, flash drive, and its corresponding disk drive) as permanent storage device 802. Like permanent storage device 802, system memory 804 is a read-and-write memory device. However, unlike storage device 802, system memory 804 is a volatile read-and-write memory, such as, random access memory. System memory 804 stores some of the instructions and data that the processor needs at runtime. In some implementations, the processes of the subject disclosure are stored in system memory 804, permanent storage device 802, and/or ROM 810. From these various memory units, processing unit(s) 812 retrieves instructions to execute and data to process in order to execute the processes of some implementations.

Bus 408 also connects to input and output device interfaces 814 and 806. Input device interface 814 enables the user to communicate information and select commands to the electronic system. Input devices used with input device interface 814 include, e.g., alphanumeric keyboards and pointing devices (also called "cursor control devices"). Output device interfaces 806 enables, e.g., the display of images generated by the electronic system 800. Output devices used with output device interface 806 include, e.g., printers and display devices, such as cathode ray tubes (CRT) or liquid crystal displays (LCD). Some implementations include devices such as a touchscreen that functions as both input and output devices.

Also, as shown in FIG. 8, bus 808 also couples electronic system 800 to a network (not shown) through network interfaces 816. Network interfaces 816 may include, e.g., a wireless access point (e.g., Bluetooth or WiFi) or radio circuitry for connecting to a wireless access point. Network interfaces 816 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 800 can be used in conjunction with the subject disclosure.

These functions described above can be implemented in computer software, firmware, or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses:

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identification Clause 1. A system for remote scanning and validating clinical order device configurations, comprising: a processor; and a non-transitory computer-readable medium including instructions that, when executed by the processor, cause the system to: receive a request for a test instance of an infusion device; cause the test instance to be created based on the request; cause an automated programming command to be transmitted to the identified test instance, the automated programming command including validation information for validating clinical order data; generate, based on the automated programming command being transmitted to the test instance, a programming response including an image, or reference to the image, of a graphical user interface that would be presented by the infusion device configured according to the validation information; and provide the programming response for storage in a records system.

Clause 2. The system of claim 1, wherein the automated programming command is received from the records system before it is transmitted to the identified test instance.

Clause 3. The infusion device of claim 1 or claim 2, wherein the instructions further cause the system to: transmit an identifier of the test instance to the records system.

Clause 4. The system of any one of claims 1 through 3, wherein causing the test instance to be created and identified comprises the system being caused to: identify the infusion device within a physical operating environment; confirm availability of the infusion device; and create an interface for communicating with the infusion device, wherein the automated programming command is transmitted to the infusion device via the interface.

Clause 5. The system of claim 4, wherein the system being caused to identify the infusion device within a physical operating environment comprises the system being caused to: query a fleet data store for an idle infusion device corresponding to the infusion device.

Clause 6. The system of any one of claims 1 through 3, wherein causing the test instance to be created comprises the system being caused to: query a fleet data store for an idle infusion device corresponding to the infusion device; determining that an idle infusion device is unavailable; and instantiate a virtual infusion device as the test instance based at least in part on the request.

Clause 7. The system of any one of claims 1 through 6, wherein the validation information identifies drug library information stored in a drug library configured for deployment by the infusion device; and wherein the instructions causing the automated programming command to be transmitted to the identified test instance comprises the automated programming command causing the test instance to be configured by the identified drug library information from a drug library deployed to the test instance.

Clause 8. The system of claim 7, wherein causing the test instance to be created and identified comprises the system being caused to: generate a virtual instance of the infusion device, the virtual instance extending a virtual communication interface for communicating with remote systems using a message protocol of the infusion device and for receiving and processing the automated programming command, wherein the test instance comprises the virtual instance, and wherein the automated programming command is transmitted to the virtual instance via the virtual communication interface.

Clause 9. The system of claim 6 or claim 8, wherein generating the programming response comprises: receiving the programming response from the virtual instance; and formatting the programming response for the records system.

Clause 10. The system of any one of claims 1 through 9, wherein generating the programming response further comprises: extracting text from the image using optical character recognition; and comparing the extracted text with expected text for a clinical order associated with the automated programming command, wherein formatting the programming response comprises updating the programming response to include a result of the comparing.

Clause 11. The system of any one of claims 1 through 10, wherein the programming response identifies one or more deviations between data stored in a pharmacy system and programming data stored within a drug library used by the test instance.

Clause 12. A method for remote scanning and validating clinical order device configurations, comprising: transmitting, to a server, a request for a test instance of an infusion device; receiving, from the server in response to the request, an identifier of the test instance; identifying clinical order data associated with a medication; causing an automated programming command to be transmitted, based on the identifier, to the test instance to validate the identified clinical order data; receiving, based on the automated programming command being transmitted to the test instance, a programming response including an image, or reference to the image, of a graphical user interface that would be presented by the infusion device based on the infusion device processing the automated programming command; identifying an error in the clinical order data based on the programming response; and provide the programming response for storage in a records system.

Clause 13. The method of claim 12, further comprising: performing an image analysis of the image; and identifying the error in the clinical order data based on the image analysis of the image.

Clause 14. The method of claim 12 or claim 13, further comprising: identifying the infusion device within a physical operating environment; confirming availability of the infusion device; and creating an interface for communicating with the infusion device, wherein the automated programming command is transmitted to the infusion device via the interface.

Clause 15. The method of any one of claims 12 through 14, wherein identifying the infusion device comprises: querying a fleet data store for an idle infusion device corresponding to the infusion device.

Clause 16. The method of claim 12, further comprising: querying a fleet data store for an idle infusion device corresponding to the infusion device; determining that an idle infusion device is unavailable; and instantiating a virtual infusion device as the test instance based at least in part on the request.

Clause 17. The method of any one of claims 12 through 116, wherein the automated programming command includes validation information identifying drug library information stored in a drug library configured for deployment by the infusion device, the method further comprising: the automated programming command causing the test instance to be configured by the identified drug library information from a drug library deployed to the test instance.

Clause 18. The method of any one of claim 12, 13 or 17, further comprising: generating a virtual instance of the infusion device, the virtual instance extending a virtual communication interface for communicating with remote systems using a message protocol of the infusion device and for receiving and processing the automated programming command, wherein the test instance comprises the virtual instance, and wherein the automated programming command is transmitted to the virtual instance via the virtual communication interface.

Clause 19. The method of claim 18, wherein generating the programming response comprises: receiving the programming response from the virtual instance; and formatting the programming response for the records system.

Clause 20. The method of any one of claims 12 through 19, further comprising: extracting text from the image using optical character recognition; and comparing the extracted text with expected text for a clinical order associated with the automated programming request, wherein formatting the programming response comprises updating the programming response to include a result of the comparing.

Clause 21. A non-transitory computer-readable medium comprising instructions that, when executed by a processor, cause an infusion device to perform the method of any one of claims 12-20.

Further Consideration:

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The predicate words "configured to", "operable to", and "programmed to" do not imply any particular tangible or intangible modification of a subject, but, rather, are intended to be used interchangeably. For example, a processor configured to monitor and control an operation, or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism.

The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

As used herein a "user interface" (also referred to as an interactive user interface, a graphical user interface or a UI) may refer to a network based interface including data fields and/or other control elements for receiving input signals or providing electronic information and/or for providing information to the user in response to any received input signals. Control elements may include dials, buttons, icons, selectable areas, or other perceivable indicia presented via the UI that, when interacted with (e.g., clicked, touched, selected, etc.), initiates an exchange of data for the device presenting the UI. A UI may be implemented in whole or in part using technologies such as hyper-text mark-up language (HTML), FLASH™, JAVA™, .NET™, C, C++, web services, or rich site summary (RSS). In some embodiments, a UI may be included in a stand-alone client (for example, thick client, fat client) configured to communicate (e.g., send or receive data) in accordance with one or more of the aspects described. The communication may be to or from a medical device or server in communication therewith.

As used herein, the terms "determine" or "determining" encompass a wide variety of actions. For example, "determining" may include calculating, computing, processing, deriving, generating, obtaining, looking up (e.g., looking up in a table, a database or another data structure), ascertaining and the like via a hardware element without user intervention. Also, "determining" may include receiving (e.g., receiving information), accessing (e.g., accessing data in a memory) and the like via a hardware element without user intervention. "Determining" may include resolving, selecting, choosing, establishing, and the like via a hardware element without user intervention.

As used herein, the terms "provide" or "providing" encompass a wide variety of actions. For example, "providing" may include storing a value in a location of a storage device for subsequent retrieval, transmitting a value directly to the recipient via at least one wired or wireless communication medium, transmitting or storing a reference to a value, and the like. "Providing" may also include encoding, decoding, encrypting, decrypting, validating, verifying, and the like via a hardware element.

As used herein, the term "message" encompasses a wide variety of formats for communicating (e.g., transmitting or receiving) information. A message may include a machine readable aggregation of information such as an XML document, fixed field message, comma separated message, JSON, a custom protocol, or the like. A message may, in some implementations, include a signal utilized to transmit one or more representations of the information. While recited in the singular, it will be understood that a message may be composed, transmitted, stored, received, etc. in multiple parts.

As used herein, the term "selectively" or "selective" may encompass a wide variety of actions. For example, a "selective" process may include determining one option from multiple options. A "selective" process may include one or more of: dynamically determined inputs, preconfigured inputs, or user-initiated inputs for making the determination. In some implementations, an n-input switch may be included to provide selective functionality where n is the number of inputs used to make the selection.

As user herein, the terms "correspond" or "corresponding" encompasses a structural, functional, quantitative and/or qualitative correlation or relationship between two or more objects, data sets, information and/or the like, preferably where the correspondence or relationship may be used to translate one or more of the two or more objects, data sets, information and/or the like so to appear to be the same or equal. Correspondence may be assessed using one or more of a threshold, a value range, fuzzy logic, pattern matching, a machine learning assessment model, or combinations thereof.

In any embodiment, data generated or detected can be forwarded to a "remote" device or location, where "remote," means a location or device other than the location or device at which the program is executed. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like.

What is claimed is:

1. A system for remote scanning and validating clinical order device configurations, comprising:
   a processor; and
   a non-transitory computer-readable medium including instructions that, when executed by the processor, cause the system to:
   receive a request for a test instance of an infusion device to validate clinical order data;

determine, based on the request, that an idle infusion device is unavailable to validate the clinical order data;

in response to an idle infusion device being unavailable, instantiate a virtual infusion device as the test instance based at least in part on the request, wherein the virtual infusion device extends a virtual communication interface for communicating with external systems using a message protocol similar or identical to a physical infusion device which it models and is configured to process automated programming commands in the same manner as the physical infusion device which it models;

cause an automated programming command to be transmitted to the virtual infusion device using the message protocol, the automated programming command including validation information for validating the clinical order data;

receive, from the virtual infusion device, based on the automated programming command being transmitted to the virtual infusion device, a programming response including an image, or reference to the image, of a graphical user interface generated by the virtual infusion device and that would be presented by the physical infusion device which it models when configured according to the validation information for validating the clinical order data, wherein the programming response indicates a failure has occurred and the image visually identifies an error indicative of the failure as it would be presented by the physical infusion device;

provide the programming response for storage in a records system;

provide, for display to a user, a user interface of results comprising one or more automated programming command failures including the failure indicated by the programming response;

responsive to a user selection of the programming response, provide the image visually identifying the error for display to the user in connection with access to an editable input field for correcting the failure;

receive a correction to the failure via the input field and update a drug library or a medication database with the correction to remove a misalignment of data that would otherwise cause an infusion device to be taken out of service for a manual correction by a clinician or technician.

2. The system of claim 1, wherein the automated programming command is received from the records system before it is transmitted to the virtual infusion device.

3. The infusion device of claim 1, wherein the instructions further cause the system to:
transmit an identifier of the virtual infusion device to the records system.

4. The system of claim 1, wherein the drug library is updated with the correction, and wherein the instructions further cause the system to:
receive, in connection with the correction, a designation of the updated drug library for deployment via a network to one or more corresponding devices employing a drug library associated with the failure; and
cause deployment of the updated drug library.

5. The system of claim 4, wherein the instructions further cause the system to:
query a fleet data store for the idle infusion device.

6. The system of claim 1,
wherein the validation information identifies drug library information stored in a drug library configured for deployment by the infusion device; and
wherein the instructions causing the automated programming command to be transmitted to the virtual infusion device comprises the automated programming command causing the virtual infusion device to be configured by the identified drug library information from a drug library deployed to the test instance.

7. The system of claim 1, wherein the instructions further cause the system to:
format the programming response for the records system.

8. The system of claim 7, wherein the instructions further cause the system to:
extract text from the image using optical character recognition; and
compare the extracted text with expected text for a clinical order associated with the automated programming command,
wherein formatting the programming response comprises updating the programming response to include a result of the comparing.

9. The system of claim 1, wherein the programming response identifies one or more deviations between data stored in a pharmacy system and programming data stored within a drug library used by the virtual infusion device.

10. A method for remote scanning and validating clinical order device configurations, comprising:
transmitting, to a server, a request for a test instance of an infusion device to validate clinical order data;
determine, based on the request, that an idle infusion device is unavailable to validate the clinical order data;
in response to an idle infusion device being unavailable, instantiate a virtual infusion device as the test instance based at least in part on the request, wherein the virtual infusion device extends a virtual communication interface for communicating with external systems using a message protocol similar or identical to a physical infusion device which it models and is configured to process automated programming commands in the same manner as the physical infusion device which it models;
identifying clinical order data associated with a medication;
causing an automated programming command to be transmitted, based on the identifier, to the virtual infusion device using the message protocol to validate the identified clinical order data, the automated programming command including validation information for validating the clinical order data;
receiving, based on the automated programming command being transmitted to the virtual infusion device, a programming response including an image, or reference to the image, of a graphical user interface generated by the virtual infusion device and that would be presented by the physical infusion device which it models when configured according to the validation information for validating the clinical order data, wherein the programming response indicates a failure has occurred and the image visually identifies an error indicative of the failure as it would be presented by the physical infusion device;
provide the programming response for storage in a records system;

providing, for display to a user, a user interface of results comprising one or more automated programming command failures including the failure indicated by the programming response;

responsive to a user selection of the programming response, providing the image visually identifying the error for display to the user in connection with access to an editable input field for correcting the failure;

receiving a correction to the failure via the input field and updating a drug library or a medication database with the correction to remove a misalignment of data that would otherwise cause an infusion device to be taken out of service for a manual correction by a clinician or technician.

11. The method of claim 10, further comprising:
performing an image analysis of the image, the image analysis including comparing the image to a reference image associated with a clinical order to determine whether the image corresponds to the reference image; and
identifying the error in the clinical order data based on whether the image corresponds to the reference image.

12. The method of claim 10, further comprising:
identifying, before transmitting the request, the infusion device within a physical operating environment.

13. The method of claim 10, wherein the drug library is updated with the correction, the method further comprising:
receiving, in connection with the correction, a designation of the updated drug library for deployment via a network to one or more corresponding devices employing a drug library associated with the failure; and
causing deployment of the updated drug library.

14. The method of claim 10, wherein the automated programming command includes validation information identifying drug library information stored in a drug library configured for deployment by the infusion device, the method further comprising:
the automated programming command causing the virtual infusion device to be configured by the identified drug library information from a drug library deployed to the test instance.

15. The method of claim 10, further comprising:
extracting text from the image using optical character recognition;
comparing the extracted text with expected text for a clinical order associated with the automated programming request; and
formatting the programming response by updating the programming response to include a result of the comparing.

16. A non-transitory computer-readable medium comprising instructions that, when executed by a processor, cause an infusion device to perform a method, comprising:
transmitting, to a server, a request for a test instance of an infusion device to validate clinical order data;
determine, based on the request, that an idle infusion device is unavailable to validate the clinical order data;
in response to an idle infusion device being unavailable, instantiate a virtual infusion device as the test instance based at least in part on the request, wherein the virtual infusion device extends a virtual communication interface for communicating with external systems using a message protocol similar or identical to the physical infusion device which it models and is configured to process automated programming commands in the same manner as the physical infusion device which it models;

identifying clinical order data associated with a medication;

causing an automated programming command to be transmitted, based on the identifier, to the virtual infusion device using the message protocol to validate the identified clinical order data, the automated programming command including validation information for validating the clinical order data;

receiving, based on the automated programming command being transmitted to the virtual infusion device, a programming response including an image, or reference to the image, of a graphical user interface generated by the virtual infusion device and that would be presented by the physical infusion device which it models when configured according to the validation information for validating the clinical order data, wherein the programming response indicates a failure has occurred and the image visually identifies an error indicative of the failure as it would be presented by the physical infusion device;

provide the programming response for storage in a records system;

providing, for display to a user, a user interface of results comprising one or more automated programming command failures including the failure indicated by the programming response;

responsive to a user selection of the programming response, providing the image visually identifying the error for display to the user in connection with access to an editable input field for correcting the failure;

receiving a correction to the failure via the input field and updating a drug library or a medication database with the correction to remove a misalignment of data that would otherwise cause an infusion device to be taken out of service for a manual correction by a clinician or technician.

17. The non-transitory computer-readable medium of claim 16, the method further comprising:
performing an image analysis of the image, the image analysis including comparing the image to a reference image associated with a clinical order to determine whether the image corresponds to the reference image; and
identifying the error in the clinical order data based on whether the image corresponds to the reference image.

18. The non-transitory computer-readable medium of claim 16, the method further comprising:
identifying, before transmitting the request, the infusion device within a physical operating environment.

19. The non-transitory computer-readable medium of claim 16, wherein the drug library is updated with the correction, the method further comprising:
receiving, in connection with the correction, a designation of the updated drug library for deployment via a network to one or more corresponding devices employing a drug library associated with the failure; and
causing deployment of the updated drug library.

20. The non-transitory computer-readable medium of claim 16, wherein the automated programming command includes validation information identifying drug library information stored in a drug library configured for deployment by the infusion device, the method further comprising:
the automated programming command causing the virtual infusion device to be configured by the identified drug library information from a drug library deployed to the test instance;

extracting text from the image using optical character recognition;
comparing the extracted text with expected text for a clinical order associated with the automated programming request; and
formatting the programming response by updating the programming response to include a result of the comparing.

\* \* \* \* \*